US011140939B2

(12) United States Patent
Hsu

(10) Patent No.: US 11,140,939 B2
(45) Date of Patent: *Oct. 12, 2021

(54) SENSOR ASSISTED HEAD MOUNTED DISPLAYS FOR WELDING

(71) Applicant: Illinois Tool Works Inc., Glenview, IL (US)

(72) Inventor: Christopher Hsu, Appleton, WI (US)

(73) Assignee: Illinois Tool Works Inc., Glenview, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/927,138

(22) Filed: Jul. 13, 2020

(65) Prior Publication Data

US 2020/0337407 A1 Oct. 29, 2020

Related U.S. Application Data

(63) Continuation of application No. 16/660,308, filed on Oct. 22, 2019, now Pat. No. 10,952,488, which is a (Continued)

(51) Int. Cl.
*A42B 3/22* (2006.01)
*G06T 1/20* (2006.01)
(Continued)

(52) U.S. Cl.
CPC ................ *A42B 3/225* (2013.01); *A61F 9/06* (2013.01); *A61F 9/067* (2013.01); *B23K 9/0953* (2013.01);
(Continued)

(58) Field of Classification Search
CPC .................................................. G06T 19/006
See application file for complete search history.

(56) References Cited

U.S. PATENT DOCUMENTS 3,555,239 A  1/1971 Kerth
3,652,824 A  3/1972 Okada
(Continued)

FOREIGN PATENT DOCUMENTS

CA  2725719 A1  6/2012
CA  2778699      11/2012
(Continued)

OTHER PUBLICATIONS

Anonymous: "Showcasing latest international developments in welding training systems", Australasian Welding Journal, vol. 59, Third Quarter, 2014, Jan. 1, 2014 (Jan. 1, 2014), pp. 1-5, XP055742728, Retrieved from the internet: URL:https://www.slv-halle.de/fileadmin/user_upload/Halle/Pressemitteilungen/Welding-training-IIW-C-XIV.pdf [retrieved on Oct. 22, 2020].
(Continued)

*Primary Examiner* — Phi Hoang
(74) *Attorney, Agent, or Firm* — McAndrews, Held & Malloy, Ltd.

(57) ABSTRACT

Sensor assisted head mounted displays for welding are disclosed. Disclosed example head mounted devices include an optical sensor, an augmented reality controller, a graphics processing unit, and a semi-transparent display. The optical sensor collects an image of a weld environment. The augmented reality controller determines a simulated object to be presented in a field of view, a position in the field of view, and a perspective of the simulated object in the field of view. The graphics processing unit renders the simulated object based on the perspective to represent the simulated object being present in the field of view and in the weld environment. The display presents the rendered simulated object within the field of view based on the position. At least a portion of the weld environment is observable through the
(Continued)

display and the lens when the display is presenting the rendered simulated object.

19 Claims, 19 Drawing Sheets

Related U.S. Application Data continuation of application No. 15/061,360, filed on Mar. 4, 2016, now Pat. No. 10,448,692.

(60) Provisional application No. 62/129,149, filed on Mar. 6, 2015, provisional application No. 62/130,316, filed on Mar. 9, 2015.

(51) Int. Cl.
*G06F 3/01* (2006.01)
*G06T 3/40* (2006.01)
*G02B 27/01* (2006.01)
*A61F 9/06* (2006.01)
*B23K 9/173* (2006.01)
*B23K 9/32* (2006.01)
*B23K 9/095* (2006.01)
*B23K 9/10* (2006.01)
*G02B 27/00* (2006.01)

(52) U.S. Cl.
CPC .......... *B23K 9/0956* (2013.01); *B23K 9/1087* (2013.01); *B23K 9/173* (2013.01); *B23K 9/32* (2013.01); *G02B 27/01* (2013.01); *G02B 27/0172* (2013.01); *G06F 3/013* (2013.01); *G06T 1/20* (2013.01); *G06T 3/40* (2013.01); *G02B 27/0093* (2013.01); *G02B 2027/014* (2013.01); *G02B 2027/0138* (2013.01); *G02B 2027/0141* (2013.01); *G02B 2027/0174* (2013.01); *G02B 2027/0178* (2013.01); *G02B 2027/0187* (2013.01); *G05B 2219/32014* (2013.01)

(56) References Cited

U.S. PATENT DOCUMENTS

| | | | |
|---|---|---|---|
| 4,021,840 A | 5/1977 | Ellsworth | |
| 4,280,137 A | 7/1981 | Ashida | |
| 4,477,712 A | 10/1984 | Lillquist | |
| 4,577,796 A | 3/1986 | Powers | |
| 4,641,292 A | 2/1987 | Tunnell | |
| 4,707,647 A | 11/1987 | Coldren | |
| 4,733,051 A | 3/1988 | Nadeau | |
| 4,812,614 A | 3/1989 | Wang | |
| 5,275,327 A | 1/1994 | Watkins | |
| 5,380,978 A | 1/1995 | Pryor | |
| 5,572,102 A | 11/1996 | Goodfellow | |
| 5,580,475 A | 12/1996 | Sakai | |
| 5,923,555 A | 7/1999 | Bailey | |
| 5,932,123 A | 8/1999 | Marhofer | |
| 5,978,090 A | 11/1999 | Burri | |
| 6,122,042 A | 9/2000 | Wunderman et al. | |
| 6,240,253 B1 | 5/2001 | Yamaguchi | |
| 6,242,711 B1 | 6/2001 | Cooper | |
| 6,572,379 B1 | 6/2003 | Sears | |
| 6,587,186 B2 | 7/2003 | Bamji | |
| 6,734,393 B1 | 5/2004 | Friedl | |
| 6,754,518 B1* | 6/2004 | Lloyd | A61B 5/0073 356/432 |
| 7,534,005 B1 | 5/2009 | Buckman | |
| 7,926,118 B2 | 4/2011 | Becker | |
| 7,962,967 B2 | 6/2011 | Becker | |
| 7,987,492 B2 | 7/2011 | Liwerant | |
| 8,224,029 B2 | 7/2012 | Saptharishi | |
| 8,274,013 B2 | 9/2012 | Wallace | |
| 8,275,201 B2 | 9/2012 | Rangwala | |
| 8,316,462 B2 | 11/2012 | Becker et al. | |
| 8,502,866 B2 | 8/2013 | Becker | |
| 8,569,655 B2 | 10/2013 | Cole | |
| 8,605,008 B1 | 12/2013 | Prest | |
| 8,680,434 B2 | 3/2014 | Stoger et al. | |
| 8,808,164 B2 | 8/2014 | Hoffman | |
| 8,826,357 B2 | 9/2014 | Fink | |
| 8,915,740 B2 | 12/2014 | Zboray | |
| 8,934,029 B2 | 1/2015 | Nayar | |
| 8,957,835 B2 | 2/2015 | Hoellwarth | |
| 8,964,298 B2 | 2/2015 | Haddick | |
| RE45,398 E | 3/2015 | Wallace | |
| 8,992,226 B1 | 3/2015 | Leach | |
| 9,056,365 B2 | 6/2015 | Hoertenhuber | |
| 9,073,138 B2 | 7/2015 | Wills | |
| 9,097,891 B2 | 8/2015 | Border | |
| 9,101,994 B2 | 8/2015 | Albrecht | |
| 9,235,051 B2 | 1/2016 | Salter | |
| 9,244,539 B2 | 1/2016 | Venable | |
| 9,352,411 B2 | 5/2016 | Batzler | |
| 9,666,160 B2 | 5/2017 | Patel | |
| 9,977,242 B2 | 5/2018 | Patel | |
| 2002/0017752 A1 | 2/2002 | Levi | |
| 2004/0034608 A1 | 2/2004 | de Miranda et al. | |
| 2004/0189675 A1 | 9/2004 | Pretlove | |
| 2005/0001155 A1 | 1/2005 | Fergason | |
| 2005/0099102 A1 | 5/2005 | Villarreal | |
| 2005/0103767 A1 | 5/2005 | Kainec | |
| 2005/0161357 A1 | 7/2005 | Allan | |
| 2005/0199605 A1 | 9/2005 | Furman | |
| 2006/0087502 A1 | 4/2006 | Karidis | |
| 2006/0176467 A1 | 8/2006 | Rafii | |
| 2006/0207980 A1 | 9/2006 | Jacovetty | |
| 2006/0213892 A1 | 9/2006 | Ott | |
| 2006/0281971 A1 | 12/2006 | Sauer | |
| 2007/0187378 A1 | 8/2007 | Karakas | |
| 2008/0083351 A1 | 4/2008 | Lippert | |
| 2008/0158502 A1 | 7/2008 | Becker | |
| 2008/0187235 A1 | 8/2008 | Wakazono | |
| 2008/0314887 A1 | 12/2008 | Stoger | |
| 2009/0014500 A1 | 1/2009 | Cho et al. | |
| 2009/0134203 A1 | 5/2009 | Domec et al. | |
| 2009/0173726 A1* | 7/2009 | Davidson | B23K 9/0956 219/130.01 |
| 2009/0231423 A1* | 9/2009 | Becker | A61F 9/06 348/82 |
| 2009/0276930 A1 | 11/2009 | Becker | |
| 2009/0298024 A1 | 12/2009 | Batzler | |
| 2010/0036624 A1 | 2/2010 | Martin | |
| 2010/0079356 A1 | 4/2010 | Hoellwarth | |
| 2010/0206851 A1 | 8/2010 | Nakatate | |
| 2010/0223706 A1 | 9/2010 | Becker | |
| 2010/0262468 A1 | 10/2010 | Blankenship | |
| 2011/0091846 A1 | 4/2011 | Kreindl | |
| 2011/0108536 A1 | 5/2011 | Inada | |
| 2011/0117527 A1 | 5/2011 | Conrardy | |
| 2011/0187859 A1 | 8/2011 | Edelson | |
| 2011/0220616 A1 | 9/2011 | Mehn | |
| 2011/0220619 A1 | 9/2011 | Mehn | |
| 2011/0227934 A1 | 9/2011 | Sharp | |
| 2011/0309236 A1 | 12/2011 | Tian | |
| 2012/0012561 A1 | 1/2012 | Wiryadinata | |
| 2012/0074114 A1 | 3/2012 | Kawamoto | |
| 2012/0152923 A1 | 6/2012 | Sickels | |
| 2012/0176659 A1 | 7/2012 | Hsieh | |
| 2012/0180180 A1 | 7/2012 | Steve | |
| 2012/0189993 A1 | 7/2012 | Kindig | |
| 2012/0229632 A1 | 9/2012 | Hoertenhuber | |
| 2012/0241429 A1 | 9/2012 | Knoener | |
| 2012/0249400 A1 | 10/2012 | Demonchy | |
| 2012/0262601 A1 | 10/2012 | Choi | |
| 2012/0291172 A1 | 11/2012 | Wills | |
| 2012/0298640 A1 | 11/2012 | Conrardy | |
| 2012/2298640 | 11/2012 | Conrardy | |
| 2013/0050432 A1 | 2/2013 | Perez | |
| 2013/0081293 A1 | 4/2013 | Delin | |
| 2013/0112678 A1 | 5/2013 | Park | |

(56) References Cited

U.S. PATENT DOCUMENTS

| | | | |
|---|---|---|---|
| 2013/0183645 A1* | 7/2013 | Wallace | A42B 3/042 434/234 |
| 2013/0189657 A1 | 7/2013 | Wallace | |
| 2013/0189658 A1 | 7/2013 | Peters | |
| 2013/0206740 A1 | 8/2013 | Pfeifer | |
| 2013/0206741 A1* | 8/2013 | Pfeifer | G01S 11/14 219/130.01 |
| 2013/0208569 A1 | 8/2013 | Pfeifer | |
| 2013/0215281 A1 | 8/2013 | Hobby | |
| 2013/0229485 A1 | 9/2013 | Rusanovskyy | |
| 2013/0234935 A1 | 9/2013 | Griffith | |
| 2013/0291271 A1 | 11/2013 | Becker | |
| 2013/0321462 A1* | 12/2013 | Salter | G06F 3/011 345/633 |
| 2013/0345868 A1 | 12/2013 | One | |
| 2014/0014637 A1 | 1/2014 | Hunt | |
| 2014/0014638 A1 | 1/2014 | Artelsmair | |
| 2014/0020147 A1 | 1/2014 | Anderson | |
| 2014/0059730 A1 | 3/2014 | Kim | |
| 2014/0063055 A1* | 3/2014 | Osterhout | G06F 3/165 345/633 |
| 2014/0092015 A1 | 4/2014 | Xing | |
| 2014/0097164 A1 | 4/2014 | Beistle | |
| 2014/0134579 A1 | 5/2014 | Becker | |
| 2014/0134580 A1 | 5/2014 | Becker | |
| 2014/0144896 A1 | 5/2014 | Einav | |
| 2014/0159995 A1 | 6/2014 | Adams | |
| 2014/0183176 A1 | 7/2014 | Hutchison | |
| 2014/0184496 A1 | 7/2014 | Gribetz | |
| 2014/0185282 A1 | 7/2014 | Hsu | |
| 2014/0205976 A1 | 7/2014 | Peters | |
| 2014/0232825 A1 | 8/2014 | Gotschlich | |
| 2014/0263224 A1 | 9/2014 | Becker | |
| 2014/0263249 A1 | 9/2014 | Miller | |
| 2014/0272835 A1 | 9/2014 | Becker | |
| 2014/0272836 A1 | 9/2014 | Becker | |
| 2014/0272837 A1 | 9/2014 | Becker | |
| 2014/0272838 A1 | 9/2014 | Becker | |
| 2014/0320529 A1 | 10/2014 | Roberts | |
| 2014/0326705 A1 | 11/2014 | Kodama | |
| 2014/0346158 A1 | 11/2014 | Matthews | |
| 2015/0009316 A1 | 1/2015 | Baldwin | |
| 2015/0056584 A1* | 2/2015 | Boulware | B23K 9/32 434/234 |
| 2015/0072323 A1 | 3/2015 | Postlethwaite | |
| 2015/0125836 A1* | 5/2015 | Daniel | G09B 19/24 434/234 |
| 2015/0154884 A1 | 6/2015 | Salsich | |
| 2015/0190875 A1 | 7/2015 | Becker | |
| 2015/0190876 A1 | 7/2015 | Becker | |
| 2015/0190887 A1 | 7/2015 | Becker | |
| 2015/0190888 A1 | 7/2015 | Becker | |
| 2015/0194072 A1 | 7/2015 | Becker | |
| 2015/0194073 A1 | 7/2015 | Becker | |
| 2015/0209887 A1 | 7/2015 | DeLisio | |
| 2015/0248845 A1 | 9/2015 | Postlethwaite | |
| 2015/0304538 A1 | 10/2015 | Huang | |
| 2015/0325153 A1 | 11/2015 | Albrecht | |
| 2015/0352653 A1 | 12/2015 | Albrecht | |
| 2015/0375324 A1 | 12/2015 | Becker | |
| 2015/0375327 A1 | 12/2015 | Becker | |
| 2015/0379894 A1 | 12/2015 | Becker | |
| 2016/0027215 A1 | 1/2016 | Burns | |
| 2016/0049085 A1 | 2/2016 | Beeson | |
| 2016/0158884 A1 | 6/2016 | Hagenlocher | |
| 2016/0183677 A1 | 6/2016 | Achillopoulos | |
| 2016/0284311 A1 | 9/2016 | Patel | |
| 2016/0365004 A1 | 12/2016 | Matthews | |
| 2017/0053557 A1 | 2/2017 | Daniel | |
| 2017/0249858 A1 | 8/2017 | Boettcher | |

FOREIGN PATENT DOCUMENTS

| | | |
|---|---|---|
| CN | 1749940 | 3/2006 |
| CN | 101067905 A | 11/2007 |
| CN | 101248659 | 8/2008 |
| CN | 101965576 | 2/2011 |
| CN | 102165504 A | 8/2011 |
| CN | 102625739 A | 8/2012 |
| CN | 103170767 | 6/2013 |
| CN | 103687687 A | 3/2014 |
| CN | 204013703 | 12/2014 |
| CN | 104384765 | 3/2015 |
| CN | 104599314 | 5/2015 |
| DE | 4313508 A1 | 10/1994 |
| EP | 0165501 | 12/1985 |
| EP | 2082656 A1 | 7/2009 |
| JP | S52126656 | 10/1977 |
| JP | 2002178148 | 6/2002 |
| JP | 2016203205 | 12/2016 |
| WO | 2008101379 A1 | 8/2008 |
| WO | 2009137379 A1 | 11/2009 |
| WO | 2013122805 A1 | 8/2013 |
| WO | 2014188244 | 11/2014 |
| WO | 20140188244 | 11/2014 |
| WO | 2015121742 | 8/2015 |
| WO | 2016044680 | 3/2016 |
| WO | 2010062481 A1 | 6/2020 |

OTHER PUBLICATIONS www.boxford.co.us: "Augmented Reality Welding Training", Commercial video from Boxford, Aug. 7, 2014 (Aug. 7, 2014); Retrieved from the Internet: URL:https://www.youtube.com/watch?v=mjJcebhlo_g [retrieved Dec. 23, 2020].

European Patent Office, Brief Communication with Oral Proceedings in Application No. 16713176.2, dated Nov. 3, 2020.

OV10642:1.3-Megapixel OmniHDRTM, http://www.ovt.com/applications/application.php?id=7 (2 pages), [retrieved on Jan. 5, 2016].

Pamian, Neda et al., Integration of a Multi-Camera Vision System and Strapdown Inertial Naviation System (SDINS) with a Modified Kalman Filter, Sensors 2010,10, 5378-5394; doi: 10.3390/s100605378 (17 pages).

Patent Cooperation Treaty, Notification of Transmittal of the International Search Report and the Written Opinion of the International Searching Authority, in PCT/US2016/020865, dated May 11, 2016,12 pages.

Pipe-Bug, Motorized & Manual Chain Driven Pipe Cutting Machines From Bug-0 Systems (4 pages).

Reverchon, J.L., et al. New InGaAs SWIR Imaging Solutions from III-VLab, New Imaging Technologies (10 pages).

Rivers, et al., Position-Correcting Tools for 2D Digital Fabrication (7 pages).

Sergi Foix et al: "Exploitation of Time-of-Flight (ToF) Cameras IRI Technical Report", Oct. 1, 2007 (Oct. 1, 2007), pp. 1-22, XP055294087, Retrieved from the Internet: URL:http://digital.csic.es/bitstream/10261/30066/1 ltime-of-flight.pdf [retrieved on Aug. 8, 2016].

Telops, Innovative Infrared Imaging, HDR-IR High Dynamic Range IR Camera, http://www.telops.com/en/infrared-cameras/hdr-ir-high-dynamic-range-ir-camera, 2015 (2 pages).

Wavelength Selective Switching, http://en.wikipedia.org/wiki/wavelength_selective_switching, Mar. 4, 2015 (5 pages).

Windows 10 to Get 'Holographic' Headset and Cortana, BBC News, www.bbc.com/news/technology-30924022, Feb. 26, 2015 (4 pages).

Bombardier et al: "Dual Digimig/Pulse Feeder and SVI-450i Power Supply", Feb. 1999 (Feb. 1999), XP055480578, Retrieved from the Internet: URL:http://www.esabna.com/eu/literature/arc%20equipment/accessories/dual%20digimig_pulse_fdr%20&%20svi-450i_15-565.pdf [retrieved on Jun. 1, 2018].

European Office Action Appln No. 16713176.2 dated Oct. 17, 2018 (7 pgs).

(56) References Cited

OTHER PUBLICATIONS

ASH VR1-DIY Homebrew PC Virtual Reality Head Mounted Display HMD, alrons1972, https://www.youtube.com/Watch?v=VOQboDZqguU, Mar. 3, 2013, YouTube screenshot submitted in lieu of the video itself.
High Dynamic Range (HDR) Video Image Processing for Digital Glass, Augmented Reality in Quantigraphic Lightspace and Mediated Reality with Remote Expert, Raymond Lo, Sep. 12, 2012, https://www.youtube.com/Watch?v=ygcm0AQXX9k, YouTube screenshot submitted in lieu of the video itself.
Optical Head-Mounted Display, Wikipedia, Jun. 2, 2016, https://en.wikipedia.org/wiki/Optical_head-mounted_display 14 pages.
Soldamatic Augmented Training, Augmented Reality World, May 30, 2013, https://www.youtube.com/watch?V=Mn0O52Ow_qY, YouTube screenshot submitted in lieu of the video itself.
"High Dynamic Range (HDR) Video Image Processing for Digital Glass, Wearable Cybernetic Eye Tap Helmet Prototype," Raymond Lo, https://www.youtube.com/watch?v=gtTdiqDqHc8, Sep. 12, 2012, YouTube screenshot Submitted in lieu of the video itself.
About Us. Weldobot.com. <http://weldobot.com/?page_id=6> Accessed Jun. 2, 2016. 1 page.
AD-081CL Digital 2CCD Progressive Scan HDR/High Frame Rate Camera User's Manual, Jul. 1, 2012 (Jul. 1, 2012) p. 27, XP055269758, Retrieved from the Internet: URL:http://www.stemmer-imaging.de/media/up loads/docmanager/53730_JAI_AD-081_CL_Manual.pdf [retrieved on Apr. 29, 2016] the whole document (55 pages).
Aiteanu, Dorin, "Virtual and Augmented Reality Supervisor for a New Welding Helmet" Nov. 15, 2005, pp. 1-150.
Altasens—Wide Dynamic Range (WDR), http://www.altasens.com/index.php/technology/wdr (1 page), [retrieved on Jan. 5, 2016].
Aiteanu et al., Generation and Rendering of a Virtual Welding Seam in an Augmented Reality Training Envionment, Proceedings of the Sixth IASTED International Conference Visualization, Imaging, and Image Proceeding, Aug. 28-30, 2006, Palma de Mallorca, Spain ISBN Hardcapy: 0-88986-598-1 /CD: 0-88986-600-7 (8 pages).
Anonymous: "JAI introduces unique high-dynamic-range camera", Nov. 5, 2009 (Nov. 5, 2009), XP055269759, Retrieved from the Internet: URL:http://www.jai.com/en/newsevents/news/ad-081c1 [retrieved on Apr. 29, 2016] Typical HDR applications for the AD-081CL include inspection tasks where incident light or bright reflections are Oresent, such as . . . welding (2 pages).
Cameron Series: "Why Weld Cameras Need Why High Dynamic Range Imaging", Apr. 10, 2013 (Apr. 10, 2013), XP055269605, Retrieved from the Internet: URL:http://blog.xids.com/blog/bid/258666/Why-Weld-Cameras-Need-High-Dynamic-Range-Imaging [retrieved on Apr. 29, 2016] the whole document (5 pages).
Cavilux HF, Laser Light for High-Speed Imaging, See What You Have Missed (2 pages).
Cavilux Smart, Laser Light for Monitoring and High Speed Imaging, Welcome to the Invisible World (2 pages).
Choi et al., Simulation of Dynamic Behavior in a GMAW System, Welding Research Supplement, Oct. 2001, 239-s thru 245-s (7 pages).
Communication from European Patent Office Appln No. 18 150 120.6 dated Jul. 4, 2018 (9 pgs).
Daqri Smart Helmet, The World's First Wearable Human Machine Interface, Brochure (9 pages).
Electronic speckle pattern interferometry Wikipedia, the free encyclopedia (4 pages), [retrieved on Feb. 10, 2015].
Frank Shaopeng Cheng (2008). Calibration of Robot Reference Frames for Enhanced Robot Positioning Accuracy, Robot Manipulators, Marco Ceccarelli (Ed.), ISBN: 978-953-7619-06-0, InTech, Available from: http://www.intechopen.com/books/robot_manipulators/calibration_of robot_reference_frames_for enhanced_r obot_positioning_accuracy (19 pages).
G. Melton et al: "Laser diode based vision system for viewing arc welding (May 2009)", EUROJOIN 7, May 21, 2009 (May 21, 2009), XP055293872, Venice Lido, Italy, May 21-22, 2009.
Handheld Welding Torch with Position Detection technology description, Sep. 21, 2011 (11 pages).

HDR Camera for Industrial and Commercial Use, Invisual E Inc., http://www.invisuale.com/hardware/hdr-camera.html (2 pages), [retrieved on Jan. 5, 2016].
Heston, Tim, Lights, camera, lean-recording manufacturing efficiency, The Fabricator, Aug. 2010 (4 pages).
Hillers, Bernd & Aiteanu, D & Tschimer, P & Park, M & Graeser, Axel & Balazs, B & Schmidt, L. (2004). TEREBES: Welding helmet with AR capabilities.
Hillers, Bernd, Iat Institut fur Automatislerungstechnik, doctoral thesis Selective Darkening Filer and Welding Arc Observation for the Manual Welding Process, Mar. 15, 2012,152 pgs.
Int' Search Report and the Written Opinion Appin No. PCT/US2016/016107, dated May 17, 2016 (11 pages).
Int'l Search Report and Written Opinion for PCT/US2015/067931 dated Jul. 26, 2016 (19 pages).
Int'l Search Report and Written Opinion for PCT/US2016/035473 dated Aug. 17, 2016 (15 pages).
Int'l Search Report and Written Opinion for PCT/US2018/028261 dated Aug. 6, 2018 (17 pgs).
Intelligent Robotic Arc Sensing, Lincoln Electric, Oct. 20, 2014, http://www.lincolnelectric.com/en-us/support/process-and-theory/pages/intelligent-robotic-detail.aspx (3 pages).
Intelligenter SchweiBbrenner, Intelligent Welding Torch, IP Bewertungs AG (IPB) (12 pages).
International Search Report and Written Opinion corresponding to International Patent Application No. PCT/US2016/012164, dated May 12, 2016.
International Search Report and Written Opinion corresponding to International Patent Application No. PCT/US2016/020861, dated May 23, 2016.
Larkin et al., "3D Mapping using a ToF Camera for Self Programming an Industrial Robot", Jul. 2013, IEEE, 2013 IEEE/ASME International Conference on Advanced Intelligent Mechatronics (AIM), pp. 494,499.
Li, Larry, Time-of-Flight Camera—An Introduction, Technical White Paper, SLOA190B—Jan. 2014, revised May 2014 (10 pages).
LiveArc Welding Performance Management System, A reality-based recruiting, screening and training solution, MillerWelds.com 2014 (4 pages).
Lutwak, Dr. Robert, DARPA, Microsystems Tech. Office, Micro-Technology for Positioning, Navigation, and Timing Towards PNT Everywhere and Always, Feb. 2014 (4 pages).
Lutwak, Dr. Robert, Micro-Technology for Positioning, Navigation, and Timing Towards PNT Everywhere and Always Stanford PNT Symposium, Stanford, CA Oct. 29, 2014 (26 pages).
Mnich, Chris, et al., "In situ weld pool measurement using sterovision," Japan-UA Symposium on Flexible Automation, Denver, CO 2004.
Ni, Y. et al. A 768x576 Logarithmic Image Sensor with Photodiode in Solar Cell Mode, New Imaging Technologies (4 pges).
Ni, Yang, et al., A CMOS Log Image Sensor with On-Chip FPN Compensation (4 pages).
NIT Color Management, R&D Report N RD1113-Rev B, Apr. 11, 2011 (31 pages).
NIT Image Processing Pipeline for Lattice HDR-6-, NIP, Pipeline, IP_NIT_NSC1005C_HDR60_V1_0 (23 pages).
NIT Image Processing Pipeline, R&D Report N RD1220-Rev B, May 14, 2012 (10 pages).
NIT, 8Care12004-02-B1 Datasheet, New Imaging Technologies (9 pages).
NIT, Application Note: Native WDRTM for your Industrial Welding Applications, www.new-imaging-technologies.com (2 pages).
NIT, Magic Technology—White Paper, Scene Contrast Indexed Image Sensing with WDR (14 pages).
NIT, NSC1005, Datasheet, Revised Nov. 2012, NSC1005 HD ready Logarithmic CMOS Sensor (28 pages).
NIT, WiDySwire, New Imaging Technologyies (7 pages).
NIT Image Processing Pipeline for Lattice HDR-60, NIP IP Pipeline, NIT_HDR60_V1_0_Pipeline_Sample (48 pages).

\* cited by examiner

SENSOR ASSISTED HEAD MOUNTED DISPLAYS FOR WELDING

RELATED APPLICATIONS

This application is a continuation of U.S. patent application Ser. No. 16/660,308, entitled "SENSOR ASSISTED HEAD MOUNTED DISPLAYS FOR WELDING," filed Oct. 22, 2019, which is a continuation of U.S. patent application Ser. No. 15/061,360, filed Mar. 4, 2016, and issued as U.S. Pat. No. 10,448,692 on Oct. 22, 2019, which claims priority from and the benefit of U.S. Provisional Patent Application Ser. No. 62/129,149, filed Mar. 6, 2015, and to U.S. Provisional Patent Application Ser. No. 62/130,316, filed Mar. 9, 2015. Each of these above listed U.S. Applications are hereby incorporated by reference in their entireties for all purposes.

BACKGROUND

Weld operators suffer from obscured vision in a harsh arc welding environment. The sharp light intensity contrast of welding arc and surroundings make it difficult to see the seam, electrode placement within the seam, torch and travel angles, liquid weld puddle shape and position, and finished weld size and position with good clarity. The problem is compounded with excessive fume and spatter conditions of certain wire, gas and welding processes. Additionally, the welding industry suffers from a lack of skilled operators and a demand for effective operator motor skills training, either in a simulated environment or on the job with real production weldments. It is also desirable to provide real-time information, instructions, process feedback and animation of desired tool motion behavior and weld outcome to aid a weld operator in welding production. It is desirable to enable less skilled and/or experienced weld operators to produce welds that pass quality inspection.

Further limitations and disadvantages of conventional approaches to welding will become apparent to one of skill in the art, through comparison of such approaches with some aspects of the present method and system set forth in the remainder of this disclosure with reference to the drawings.

SUMMARY

Methods and systems are provided for a mediated reality welding user interface, substantially as illustrated by and/or described in connection with at least one of the figures, as set forth more completely in the claims.

Methods and systems are described on augmented reality or mixed reality with see-through or transparent displays that blend computer generated graphics with real welding scene observed directly by human eyes.

DETAILED DESCRIPTION

Figure 1:
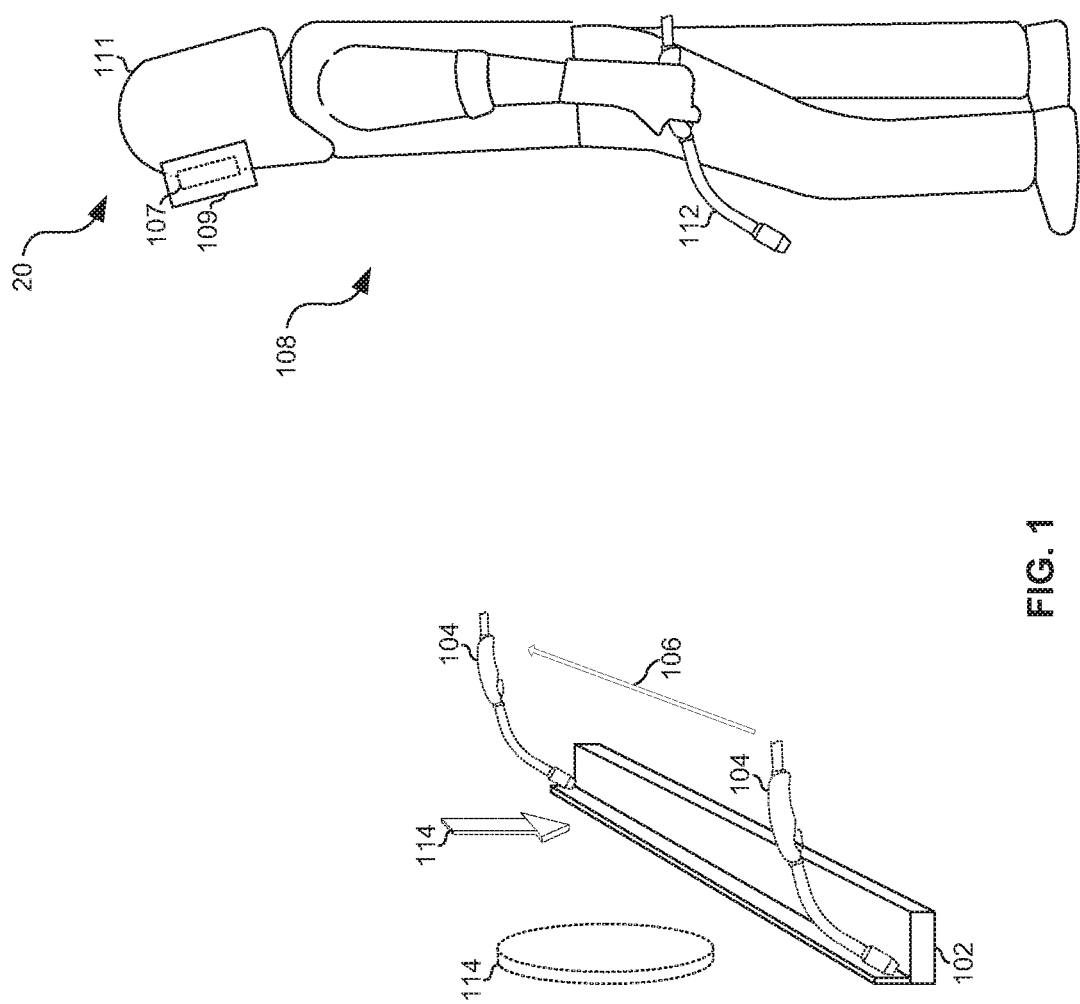
FIG. 1 illustrates example operations of an optical head mounted display (OHMD) for welding operable to render 3D augmented reality images before, during, and after welding operations.

Aspects of certain embodiments of this disclosure enhance the human welder perception of reality in an improved vision. Aspects of certain embodiments of this disclosure provide replacements for and/or improvements to auto-darkening lens systems which, although they protect the eyes from intense arc, they also darken the surroundings making it difficult for the operator to see the workpiece, the surrounding environment, etc. Aspects of certain embodiments of this disclosure improve weld operator vision without replacing it entirely with virtual reality (VR) technology, which can cause VR sickness such as simulator and motion sickness, and loss of fidelity from other image digitization effects such as spatial resolution, 2D display, time latency from real time event, color depth, parallax and aliasing, relative to direct viewing biologically. Aspects of certain embodiments of this disclosure annotate physical/real objects seen with virtual/holographic 3D objects that are spatially anchored to the real object, rather than a simple 2D data overlay.

As used herein, the terms hologram and/or holographic refer to stereographic display having a 3D imaging effect such as computer generated image content with holographic interference patterns, and does not necessarily require projection by laser, using diffraction and/or interference. For example, 3D holographic images may be produced by a dual projector system, with two stacked projectors disposed at a wearer's adjustable inter-pupillary distance.

Aspects of certain embodiments of this disclosure utilize a holographic image processing and display system to specifically to enhance weld operator user interface using an application programming interface of the image processing and display system. Aspects of certain embodiments of this disclosure provide better training, service, instructions and even welding remotely.

Aspects of certain embodiments of this disclosure provide a user interface comprising of augmented reality user interface operable to render scenes comprising a mix of physical/real objects and holograms, where the holograms track the real objects in the presence of movement, obstructions, and/or the like.

Aspects of certain embodiments of this disclosure provide a human welder user interfaces comprising one or more a of holographic near-eye display (e.g., light field display of micro lens array, etc.), and energy efficient high FOV depth camera, a head tracking sensor, a gaze tracking sensor, and one or more processors (e.g., a central processing unit, a graphics processing unit, and a holographic processing unit) for processing the data from the camera(s) and various sensors to perform, for example, spatial mapping, gesture recognition, wearable user interface, and voice and speech recognition.

Aspects of certain embodiments of the disclosure comprise a time-of-flight (ToF) depth camera operable to geometrically and dimensionally map a welding scene in 3D, a near-eye display, and associated optics and circuitry operable to render a mixed physical and virtual view to a weld operator.

Aspects of certain embodiments of this disclosure comprise an augmented reality computing device that takes the input from ToF depth camera or laser scanner or structured light or stereo vision mapping of physical objects and pins virtual 3D objects, holograms and/or annotations onto the physical locations of the real objects despite the movement of the wearer (head or eyes) and/or the physical objects.

As described below, disclosed examples include generating and displaying virtual objects to a weld operator. Virtual objects may be generated and displayed on a head mounted device to, among other things: 1) enhance the clarity of real objects in a welding scene (e.g., by displaying a clear virtual outline of an actual object, virtual obstruction removal, seeing through fume, etc.); 2) provide instruction on desired weld tool orientation and/or weld tool movement as a real-time guidance and/or coaching tool; 3) simulating a weld arc, a weld puddle, and/or a weld bead during a practice weld using a real weldment that is to be fabricated and/or during operator training; 4) superimpose or project a virtual desired weld pool, a virtual wire, a virtual non-consumable electrode, and/or a weld pool marker over a real weld scene during actual live welding for operator guidance in adjusting torch position, wire position, and/or travel speed; 5) superimpose a substantially opaque arc object to dim or reduce brightness of selected physical object such as the arc; 6) track student operator gaze for training purposes and annotate weld scene to draw the student's attention; 7) measure and display key dimensions of physical objects (e.g. puddle size, contact tip to weld distance (CTWD), arc length); 8) virtually fit components onto a weldment being welded for geometric dimensioning and tolerancing (GD&T); 9) simulate welding during weld practice on test coupons in a practice environment with a virtual fabrication component; and/or 10) simulate a weld scene to an operator performing welding via a remote welding device at the weld scene. While examples of virtual objects are disclosed below to accomplish one or more of these purposes, other virtual objects may additionally or alternatively be used.

Disclosed example head mounted devices include optical and non-optic sensor(s), an augmented reality controller, a graphics processor, and a display. The optical sensor collects a first image of a weld environment, such as a weld cell inside a factory, or a weld zone in outdoor construction or fabrication. Based on the first image of the weld environment and weld instructions that correspond to the weld environment, the augmented reality controller determines a simulated object to be presented in a field of view, a position of the simulated object in the field of view, and a gaze-adaptive perspective of the simulated object in the field of view. The simulated object is representative of an object being present in the field of view and in the weld environment. The graphics processor generates a secondary image representing the simulated object, where the secondary image includes the simulated object in the position and having the perspective determined by the augmented reality controller, and the secondary image is overlaid on the field of view. The display presents the secondary image within the field of view. At least a portion of the weld environment is observable through the display when the display is presenting the second image.

Disclosed example methods include accessing, with a processor from a storage device, weld instructions corresponding to a weld to be performed in a weld environment. The example methods also include generating, with the processor, a first image of the weld environment based on first input from an optical sensor attached to a head mounted device. The example methods also include calculating, with the processor, a position of a simulated object within the weld environment based on the weld instructions (such as Weld Procedure Specification or WPS) and a field of view through a display device of the head mounted device and calculating, with the processor, a perspective of the simulated object based on the weld instructions and the field of view. The example methods also include generating, with the processor, a second image of the simulated object to augment the field of view with a view of the simulated object, the generating of the second image being determined using the position and the perspective and displaying, on the display device, the second image of the simulated object.

Disclosed welding interface devices include an optical sensor, an augmented reality controller, a graphics processing unit, and a semi-transparent display. The optical sensor collects an image of a weld environment. The augmented reality controller, based on the image of the weld environment and first instructions that correspond to a weld operation in the weld environment, determines a simulated object to be presented in a field of view, a position of the simulated object in the field of view, and a perspective of the simulated object in the field of view. The graphics processing unit renders the simulated object based on the perspective to represent the simulated object being present in the field of view and in the weld environment. The semi-transparent display presents the rendered simulated object within the field of view based on the position determined by the augmented reality controller, where at least a portion of the weld environment is observable through the semi-transparent display when the display is presenting the rendered simulated object.

Some example welding user interface devices further include a body to house the optical sensor and the display. Some example welding user interface devices further include a lens attached to the body, where the lens reduces an intensity of light occurring in the weld environment. In some examples, the lens is arranged to provide the field of view to a wearer of the welding user interface device when the welding user interface device is worn by the wearer, and the display is a near-eye display that is positioned between the lens and the wearer of the welding user interface device when worn by the wearer. In some examples, the body is at least one of a weld operator personal protective equipment, a hard hat, an eye protector, or a face protector.

Some example welding user interface devices further include a body, where the optical sensor, the graphics processing unit, and the display are attached to the body, and the body is dimensioned to, when worn by a wearer, enable the wearer to further wear a welding helmet. In some examples, the augmented reality controller renders a view of the simulated object when viewing of a second object present in the weld environment is obscured to the field of view.

In some examples, the augmented reality controller generates the simulated object to identify a next weld to be performed based on a current weld being performed and a specified weld sequence. In some examples, the optical sensor includes a filter configured to mitigate radiation at an arc radiation wavelength. Some example welding user interface devices further include an illuminator to output second radiation at a second wavelength outside of an arc radiation spectrum, where the optical sensor includes a time-of-flight sensor to collect third signals at the second wavelength to generate the image, and the filter includes a bandpass filter to mitigate light at wavelengths other than the second wavelength.

In some examples, the graphics processing unit comprises a holographic processing unit. In some examples, the simulated object includes at least one of a weld pool, a finished weld bead, an electrode, an electrical arc, a laser path, a shielding gas path, a powder path, a weld tool, a weld bead, a weld joint, a weld fixture, a weldment or parts to be fitted or assembled onto the weldment after welding. In some examples, the simulated object includes an electrical arc, the graphics processing unit to render the simulated object to be at least partially opaque and the position corresponding to a portion of the field of view in which an actual electrical arc is present in the weld environment. In some such examples, the display displays the rendered simulated object to reduce an intensity of light from the actual electrical arc that is observable to a wearer of the welding user interface device.

In some examples, the graphics processing unit renders a zoomed view of a portion of the field of view, and the augmented reality controller determines the portion of the field of view based on at least one of the image or input from a gaze tracker. In some examples, the augmented reality controller determines the position of the zoomed view of the portion of the field of view as a corner of the field of view.

In some example welding user interface devices, the optical sensor collects a third image of the weld environment, the augmented reality controller updates the position and the perspective of the simulated object based on the third image of the weld environment, and the graphics processing unit renders the simulated object based on the update to the position and the perspective by the augmented reality controller. Some example welding user interface devices further include a communications controller to communicate a disable command in response to identifying a deviation from the first instructions, where the disable command causes at least one of a welding torch, a welding power source, or a welding wire feeder to be disabled. In some examples, the augmented reality controller is to determine a status of a weld being performed and compare the status to the first instructions, where the augmented reality controller determines the position and the perspective of the simulated object based on the comparison.

In some examples, the optical sensor includes a three-dimensional laser scanner, structured light sensor, time of flight camera, and/or stereo vision cameras, and the first image is a three-dimensional depth map. Some example welding user interface devices further include a communications interface to receive data representative of a weld being performed, where the graphics processing unit renders a graphic representing the data and the display to present the graphic. In some examples, the graphics processing unit includes a holographic processor.

In some examples, the augmented reality controller includes a first coprocessor and the graphics processing unit includes a second coprocessor. Some example welding user interface devices further include an inertial measurement unit to provide at least one of movement information or orientation information corresponding to the field of view, where the augmented reality controller determines at least one of the position of the simulated object or the perspective of the simulated object based on the at least one of the movement information or the orientation information.

In some examples, the first instructions correspond to a welding operation to be performed, and the augmented reality controller determines that a view of a first physical object in the weld environment is at least partially blocked based on analyzing the image, the graphics processing unit to render the simulated object to include at least a blocked portion of the first physical object. In some examples, the first instructions correspond to an electrical arc being present in the field of view, and the augmented reality controller determines the simulated object to be at least one of an electrode, a torch, a weld puddle, a weld bead, or a seam to be welded based on the electrical arc reducing visibility of the weld environment.

In some examples, the first instructions correspond to a portion of a subsequent welding operation that is to be performed after a current welding operation is complete, and the augmented reality controller determines the simulated object to correspond to a location of the subsequent welding operation on a workpiece. In some examples, the first instructions correspond to a physical object in a second weld environment, the first instructions including a second location and a second perspective of the physical object in the second weld environment, and the augmented reality controller determines the location based on the second location and determine the perspective based on the second perspective.

In some examples, the first instructions correspond to a simulated environment of a workpiece, and the augmented reality controller determines that the simulated object represents an object in the simulated environment. In some such examples, the object is a physical object in the weld environment or a holographic object in the weld environment. In some examples, the first instructions correspond to cutting procedure, and the augmented reality controller determines that the simulated object is at least one of a simulated laser envelope, a simulated gas envelope, or a simulated cut outline.

Disclosed example methods to augment a view of a weld environment include accessing first instructions corresponding to a weld operation to be performed in a weld environment, generating images of the weld environment using an optical sensor attached to a head mounted device, and calculating a position of a simulated object within the weld environment based on the first instructions and a field of view through a semi-transparent display device of the head mounted device. The simulated object is representative of an object being virtually present in the field of view and in the weld environment. The example methods further include calculating a perspective of the simulated object based on the first instructions and the field of view, rendering the simulated object to augment the field of view with a view of the simulated object. The rendering is based on the position and the perspective. The example methods further include displaying the rendered simulated object on the semi-transparent display device so that at least a portion of the weld environment is viewable through the display device when the rendered simulated object is displayed.

Some example methods further include receiving a weld parameter and displaying the weld parameter on the display device. Some example methods further include determining a change in the field of view based on the images from the optical sensor and calculating a second perspective of the simulated object within the weld environment based on the change in the field of view. The position of the simulated object within the weld environment is constant. Some example methods further include rendering the simulated object corresponding to the position and the second perspective to generate a second rendering of the simulated object and displaying, on the semi-transparent display device, the second rendering of the simulated object.

Some example methods further include determining a change in the field of view based on the images from the optical sensor, calculating a second perspective of the simulated object within the weld environment based on the change in the field of view, calculating a second position of the simulated object within the weld environment based on the first instructions, rendering the simulated object corresponding to the second position and the second perspective to generate a second rendering of the simulated object, and displaying, on the semi-transparent display device, the second rendering of the simulated object. In some examples, the generating of the images of the weld environment includes converting time-of-flight data to the images.

FIG. 1 illustrates example operations of a head mounted system 20 for welding operable to render 3D holographic images before, during, and after welding operations. Shown is a person 108 wearing head mounted system 20, a physical (i.e., actual) welding torch 112, a physical workpiece 102, virtual torch 104, and virtual objects 114. In an example implementation, the head mounted system 20 may comprise a single integrated unit with protective shell 111 and optical head mounted display 109 (OHMD). In another example implementation, the OHMD 109 may be used in conjunction with and/or integrated into a welding helmet having a shell 111 and auto-darkening lens 107 and a separate OHMD 109 which may mount to the shell 111 and over (or under) the lens 107. In various example implementations, the head mounted system 20 may comprise any combination of one or more of a helmet, a mask, goggles, glasses, a hard hat with eye protection, a helmet attachment, a mask attachment, a goggle attachment, and/or the like.

The scenario shown in FIG. 1 may be, for example, prior to the wearer 108 using torch 112 to weld workpiece 102. In this scenario, the head mounted system 20 (e.g., via the OHMD 109) may, for example, present an instructional/training holographic image or video of the virtual torch 104 welding the workpiece 102 in the manner in which the welding equipment operator is to weld the workpiece 102. The image or video may be based, for example, on computer-aided design (CAD) models for the workpiece 102, the finished weld on the workpiece (not shown), welding work instructions for the workpiece 102, and/or other data about the work retrieved from local and/or remote (e.g., on a networked server, in a cloud data center, etc.) storage. For example, the holographic image or video may show the virtual torch 104 passing the workpiece in the direction indicated by arrow 106, and having appropriate parameters (e.g., travel angle, work angle, travel speed, contact-tip-to-work distance, and/or aim or wire placement) at various points along the seam as it makes the pass. In this pre-weld instructional scenario, the virtual objects 114 may, for example, provide additional information about the weld to be performed. For example, objects 114 may provide text instructions describing the actions being performed by the virtual torch 104 and/or providing advice, warnings, clamp engagement, pre-heat, surface cleaning and tack weld reminders, notes previously taken by a welding equipment operator working on a similar workpiece, etc. As another example the objects 114 may comprise actual photographs of previous welds performed on similar workpieces. The virtual objects 114 may provide controls that the wearer 108 can virtually interact with to control what s/he sees. For example, the objects may be fast forward, rewind, pause, play, etc. controls that the wearer 108 can virtually interact with (through gesture recognition, wearable user interface, voice recognition, physical controls, and/or the like) to control the playback of the virtual welding operation. The virtual objects 114 may, for example, provide graphical representations (e.g., charts, meters, etc.) of welding parameters (such as torch angles, speed, aim, etc.) and/or welding equipment settings (e.g., voltage, amperage, wire speed) of the virtual torch as it performs the virtual weld.

As another example, the scenario shown in FIG. 1 may be after the workpiece 102 has been welded. In this scenario, the head mounted system 20 may present a recording of the welding operation performed on the workpiece 102. This enables the wearer 108 (who may be the welding equipment operator who performed the weld or an instructor, inspector, or the like) to review the weld operation to, for example, inspect for possible quality issues. The virtual objects 114 may, for example, provide additional information about the weld that was performed. For example, objects 114 may provide text describing aspects of the weld that were done properly and those that were not. As another example the objects 114 may comprise actual photographs of the completed weld (e.g., with the arc and/or other obstructions removed so the wearer 108 can clearly see, for example, what was happening in the weld puddle during the weld). The virtual objects 114 may provide controls that the wearer 108 can virtually interact with to control what s/he sees. For example, the objects may be fast forward, rewind, pause, play, etc. controls that the wearer 108 can virtually interact with (through gesture recognition, voice recognition, wearable user interface, physical controls, and/or the like) to control the playback of the recorded welding operation. The virtual objects 114 may, for example, provide graphical representations (e.g., charts, meters, etc.) of welding parameters (such as torch angles, speed, aim, etc.) and/or welding equipment settings (e.g., voltage, amperage, wire speed) of the that are time synchronized to the playback of the recording. In this manner, the wearer 120 could, for example, virtually touch a portion of the completed weld bead to cause the video to seek to the point of the recording at which the touched portion of the weld bead was laid down and cause the virtual objects 114 to display the equipment settings, torch parameters, etc. that were present at the time the touched portion of the weld bead was laid down. Alternatively, the virtual object could be a 3D virtual torch in the proper orientation relative to the workpiece 102 (e.g. work angle and travel angle) and position to achieve the desired results, that is different than the recorded torch movement. Both desired and actual virtual torches can be animated together in the playback on the real seam to contrast the difference or gap for improvement.

In another example scenario, the virtual torch 104 and objects 114 may be rendered and presented to the wearer during welding of the workpiece 102. For example, the virtual torch 104 may provide a guide for welding parameters such as torch angles, speed, aim, etc. during the welding operation such that the goal is for the wearer 108 to keep the real torch 112 aligned in three dimensions with the virtual torch 104 as the weld progresses. As another example the virtual objects 114 may present real-time visual feedback such as actual torch angles, torch speed, contact tip to work distance, welding equipment settings, etc. during a welding operation. As discussed below, the head mounted system 20 may provide an outline or wire-frame model of the important objects superimposed on the real objects such that the wearer 108 can simultaneously see both the arc/puddle and points of the workpiece 102 at a distance from the arc which would normally be too dark through the auto-darkening lens when the arc is present, or physically obstructed due to the viewing angle.

Figure 2A:
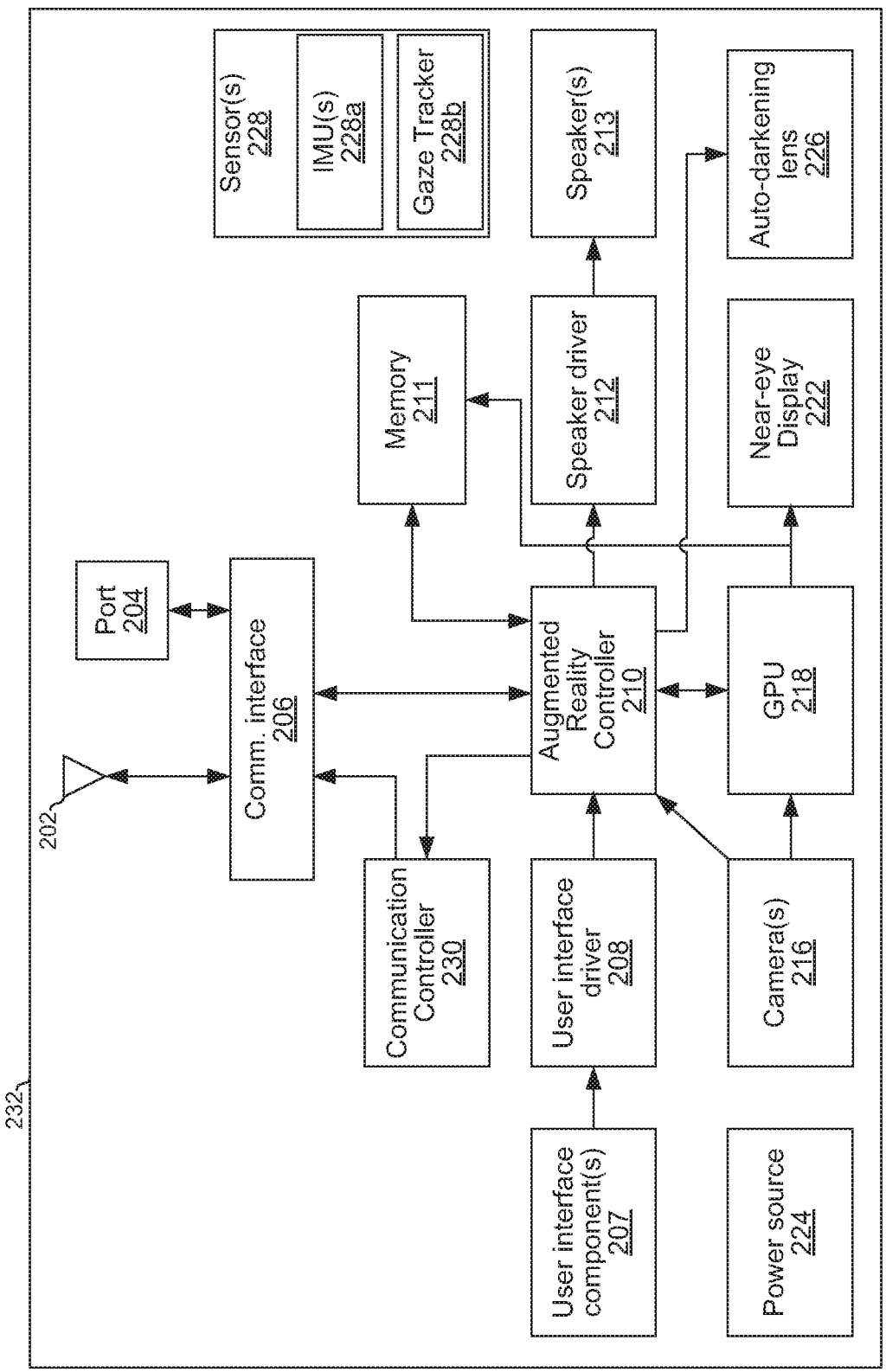
FIGS. 2A, 2B, and 2C illustrate example circuitry of the OHMD of FIG. 1 for welding.

Referring to FIG. 2A, an example implementation of head mounted system 20 is shown. In the example implementation, the head mounted system 20 comprises circuitry including: one or more optical sensor(s) 216 (e.g., cameras), a near-eye display 222, electromechanical user interface components 207, an antenna 202, a communication port 204, a communication interface 206, a user interface driver 208, an augmented reality controller 210, speaker driver circuitry 212, speaker(s) 213, a graphics processing unit (GPU) and/or holographic processing unit (HPU) 218, display driver circuitry 220, power source 224, an optional auto-darkening lens 226, sensor(s) such as inertial measurement unit (IMU) sensors for head tracking 228, and a communications controller 230. The head mounted system 20 also includes a body or shell 232, to which the optical sensor(s) 216 such as outward facing 3D depth camera (e.g. ToF or structured light), outward facing optical camera(s) and inward facing gaze tracking devices, the near-eye display 222, the optical components to support the near-eye display as holographic projector(s), the electromechanical user interface components 207, the antenna 202, the communication port 204, the communication interface 206, the user interface driver 208, the augmented reality controller 210, the speaker driver circuitry 212, the speaker(s) 213, the graphics processing unit (GPU) and/or the holographic processing unit (HPU) 218, the display driver circuitry 220, the power source 224, an optional auto-darkening lens 226, the IMU sensors 228, and/or the communications controller 230 may be attached or mounted.

Antenna 202 may be any type of antenna suited for the frequencies, power levels, etc. used for radio frequency (RF) wireless communications (e.g., Wi-Fi, WiFi hotspot or MiFi, Bluetooth, Bluetooth Low Energy, Zigbee, NFC, cellular network, PAN/WPAN, BAN and/or the like) between the head mounted system 20 and other devices such as wireless access point (WAP), welding equipment, wireless base stations, phones, computers, etc.

Communication port 204 may comprise, for example, an Ethernet port, a USB port, an HDMI port, a fiber-optic communications port, a FireWire port, a field bus port, a fiber optics port, and/or any other suitable port for interfacing with a wired or optical cable via which the head mounted system 20 may communicate with other devices such as welding equipment, wireless base stations, phones, computers, etc.

Communication interface circuitry 206 is operable to interface the augmented reality controller 210 to the antenna 202 and the port 204 for transmit and receive operations. For transmit operations, communication interface 206 receives data from augmented reality controller 210, and packetizes the data and converts the data to physical layer signals in accordance with protocols in use by the communication interface 206. The data to be transmitted may comprise, for example, control signals for controlling the torch 112. For receive operations, communication interface 206 receives physical layer signals via antenna 202 or port 204, recovers data from the received physical layer signals (demodulate, decode, etc.), and provides the data to augmented reality controller 210. The received data may comprise, for example, commanded settings and/or actual weld process signals and feedbacks measured by the equipment 12 and/or other sensors (e.g., voltage, amperage, wire speed settings and/or measurements, power, heat input, and/or logic state in weld process control state machine). Signals output to communication interface 206 may comprise, for example, signals to control the settings of equipment 12. Such signals may be generated based on signals from GPU 218 and/or the user interface driver 208. Signals from communication interface 206 comprise, for example, indications (received via antenna 202, for example) of commanded settings and/or actual weld process signals.

The electromechanical user interface components 208 may comprise, for example, one or more touchscreen elements, speakers, microphones, physical buttons, etc. that generate electric signals in response to user input. As described below, user interaction with the head mounted system 20 may additionally, or alternatively, be through gestures captured by camera(s) 216 and detected through image processing algorithms performed by the GPU 218.

User interface driver circuitry 208 conditions (e.g., debounce, filter, digitize, etc.) signals from user interface components 208 for conveyance to the augmented reality controller 210.

The augmented reality controller 210 processes data from communication interface 206, user interface driver 208, and GPU 218, and to generate control and/or data signals to be output to speaker driver circuitry 212, GPU 218, and communication interface 206. The augmented reality controller 210 may execute instructions stored in memory 211 and/or read and write data to and from memory 211. The memory 211 may include any type of volatile and/or non-volatile machine-readable storage device (e.g., random access memory, read only memory, hard disk, flash memory, etc.). In some examples, the augmented reality controller 210 includes the memory 211, the GPU 218, the sensor(s) 228, and/or the user interface driver 208, such as in a system-on-chip (SoC) implementation.

In some examples, the augmented reality controller 210 loads or accesses weld instructions (e.g., from the memory 211, from the communications interface 206, etc.) that correspond to a weld environment and/or to a weld that is to be performed or simulated. The augmented reality controller 210 also receives one or more images from one or more optical sensor(s) such as the camera(s) 216. The augmented reality controller 210 determines one or more simulated object(s) to be presented in a field of view through the auto-darkening lens 226. For example, the simulated object(s) may include a weld pool, a finished weld bead, a wire, an electrical arc, a weld joint, a weld fixture, a weldment, components to be assembled after welding, material to be removed in post weld machining, and/or any other desired object or processing. Example weld instructions indicate a desired position of a weld, a position of a workpiece in the weld environment, and/or any other information describing the weld to be performed. Virtual assembly using virtual components in post-weld operations downstream may facilitate geometric dimensioning and tolerancing (GD&T) checks on work-in-process weldment, such as to examine the effect of tolerance stack-up and/or distortion. Based on the weld instructions and the received image(s), the example augmented reality controller 210 determines a position of the simulated object in the field of view and determines a perspective of the simulated object in the field of view.

Speaker driver circuitry 212 conditions (e.g., convert to analog, amplify, etc.) signals from augmented reality controller 210 for output to one or more speakers 213. The speakers 213 may use spatial sound to simulate sound emanating from specific location (e.g. from a virtual welding arc) in the scene.

The power source 224 may comprise, for example, a battery, circuitry for charging the battery from an AC and/or DC power source, and circuitry for conditioning/delivering energy from the battery to the other circuitry of the head mounted system 20.

In an example implementation, the camera(s) may be based on time-of-flight or ToF depth or distance measurement camera, illuminating the scene with an actively modulated light source such as laser or light pulse and measuring the phase shift between the illumination and reflection, and/or time-of-flight of a light signal between the camera and the subject for each point of the image. In this type of camera, the entire scene is captured at once. In another example implementation, the camera(s) 216 may be a 3D laser scanner or structured light, which may be used to scan objects and produce a 3D drawing or model, often used for reverse engineering of a physical component/part. Yet another example implementation is two cameras spaced apart to provide stereo vision and depth perception with more complex image processing and possibly slower frame rate. ToF camera may perform well in both low-light and bright-light conditions (which helps for viewing the welding arc), may involve lower complexity to implement, provide faster response time (higher frame rate), be compact, cost-effective, and without moving parts. Structured light, however, may provide higher spatial resolution and/or depth accuracy than a ToF camera. The camera(s) 216 may provide, for example, sub-millimeter depth accuracy and 160 fps (or higher) frame rate. Since the depth measurement is extracted from phase shift for ToF, the intensity contrast between the arc and the surrounding may have less effect on the measurement than when using structured light. In some examples, the camera(s) 216 are configured with a filter that mitigates light at the arc light wavelength(s) (or spectrum).

The ToF camera imager may have CMOS pixel array designed to respond to the spectrum of the illumination light source so that the arc light and emission can be significantly attenuated (or not responded to by the imager), thus achieving much improved signal to noise ratio. The light source may be LED or laser diode, for example. For example, studies have shown that in pure argon GTAW welding, 10% $CO_2$ 90% argon blend GMAW welding and 5% $O_2$ 95% argon welding of steel, the near infrared spectra of arc shows peak intensity around 914 nm. Therefore, if the illuminating laser is set at 980 nm wavelength, thus having a longer wavelength than the peak arc intensity wavelength, or 850 nm, thus having shorter wavelength than the peak arc intensity wavelength, the system may effectively block out the visible and near infrared arc spectrum and have reliable 3D mapping of the welding scene. Another benefit of using reflected light is that solid objects reflect light, but gaseous media such as arc plasma do not reflect the light. The arc object does not reflect the illumination light as well as solid objects like welding wire (before and after being melted), molten metal in flight, spatter balls, contact tip, joint, weld pool surface and weld seam etc. Therefore the arc is almost invisible to the depth sensing TOF camera. However, arc light does provide a power level of illumination, potentially much higher than the power of ToF illumination light source. Use of a non-integrating ToF sensor that does not integrate light over time and that uses a near infrared detector (such as InGaAs) to capture the reflected short laser pulse, is one example solution to this problem. The depth resolution may be improved by adaptively increasing the laser power in areas of the scene where arc is present, with the intensity information used as a confidence metric to improve accuracy with imaging process algorithms such as Kalman filter.

Graphics processing unit (GPU) 218 is a graphics processor that processes pixel and/or other image data. In the example of FIG. 2A, image processing includes processing of pixel data from camera(s) 216 and the generation of pixel data for output to the near-eye display 222 via driver 220. Although the GPU 218 performs holographic processing in an example implementation, in another implementation there may be a dedicated holographic processing unit (HPU) working in conjunction with the GPU 218.

The example augmented reality controller 210 and the GPU 218 may be implemented using separate and discrete processors, co-processors, and/or a same processor. In the example of FIG. 2A, the augmented reality controller 210 and the GPU 218 are installed in the body 232 of the head mounted system 20. In other examples, the augmented reality controller 210 and/or the GPU 218 are external to the body 232 of the head mounted system 20 and communicate with the components that are mounted to the body 232 of the head mounted system 20 via the communication interface 206 (e.g., via the port 204 and a wired connection, and/or via the antenna 202 and a wireless connection).

In some examples, the augmented reality controller 210 determines a status of a weld being performed (e.g., via the sensors 228, communications received via the communications interface 206, and/or the camera 216) and compares the status to the weld instructions. The augmented reality controller 210 determines the position and the perspective of the simulated object based on the comparison.

Processing of pixel data from camera(s) 216 may comprise, for example, analyzing the pixel data to detect gestures, position, and the like of a wearer of the head mounted system 20. This may include, for example, correlating the gestures/position of the wearer with the virtual position of rendered holographic objects to detect when the wearer is interacting with such user interface objects. A determination that the wearer is interacting with a holographic object may, for example, result in a signal to augmented reality controller 210 such that an appropriate response to the interaction can be taken.

Generation of pixel data for output to the display driver 220 may comprise, for example, rendering image data (3D CAD models, comprising text, graphics, still photos, and/or videos) retrieved from memory 211 to produce 3D holographic objects. Determined position information of the surrounding environment may, for example, be used during rendering so that the holographic images appear to the wearer to be on or in particular locations in the surrounding environment with context-aware fitness.

The near-eye display 222 may include, for example, a near-eye light field display, a reflective micro-display, a digital micro-mirror device, a virtual retinal display, a liquid crystal on silicon (LCoS) display, a holographic display, a LCoS phase-only holographic display, a ferroelectric LCoS display, a transmissive/back-lit/front-lit/transflective liquid crystal display (LCD), an organic light emitting diode (OLED) display, a light modulator, a microlens array, a digital light processing display (DLP), an interferometric modulator display (IMOD), a field emission display (FED), a PicoP display from Microvision, a display containing electrochromic material such as tungsten oxide, a display containing suspended particles, an electronic paper display, a display with sapphire substrate and/or any other suitable type of display operable to convert electrical signals into optical signals viewable by a wearer of head mounted system 20 and superimposed on the views of the real world. Example near-eye display devices that may be used to implement the near-eye display 222 are described in U.S. Pat. No. 9,097,891, issued Aug. 4, 2015. The entirety of U.S. Pat. No. 9,097,891 is incorporated herein by reference. In an example implementation, the near-eye display 222 allows the wearer to directly see the surrounding physical environment with the optoelectronic reconstructed holographic images overlaid on the view (this may be referred to as "augmented reality"). The virtual objects are blended in the proper locations and orientation of real scene based on the 3D measurement from depth cameras.

Auto-darkening lens 226 comprises a lens (e.g., a single cell LCD sandwiched between glass and a polarizer, having a transparency that varies based on a control signal provided by augmented reality controller 210 and/or by a photodiode sensor 228. In this manner, when the welding arc is present the lens may be darkened to protect the wearer's eyes and when the welding arc is not present the lens may be lightened so that wearer can see his/her surrounding environment. A photodiode may be wired to control the near-eye display 222 directly and/or via the augmented reality controller 210 and/or the GPU 218 to create an auto-darkening effect in the near-eye display 222, instead of relying on the auto-darkening lens 226 for the darkening. Although display 222 may be controlled to have the auto-darkening effect of 226 for the purpose of viewing, 226 may be still needed to protect the exposed skin from arc exposure such as coatings to block ultraviolet and infrared and intense arc light. Some display technologies mentioned above such as a display containing electrochromic material may be used to create the auto-darkening effect as part of holographic display without an additional physical auto-darkening lens 226 as described in this paragraph.

One example way to package the components 202-232 of FIG. 2A is to integrate the components 202-232 within one helmet (e.g., the head mounted system 20 including the shell 111 of FIG. 1). Another example way to package the components 202-232 of FIG. 2A is to package the different groups of the components 202-232 separately. For example, the auto-darkening lens 226 may be included in a welding helmet and the remaining components 202-224, 228, 230 may be packaged into a second wearable device. Alternative packaging may also be used. Packaging groups of the components 202-232 separately may provide cost benefits if, for example, the augmented reality/holographic wearable device is produced in high volume for applications other than welding.

The sensor(s) 228 may comprise, for example, a charge-coupled device, a black silicon sensor, an IR sensor, an acoustic sensor, an induction sensor, a motion sensor, an optical sensor, an opacity sensor, a proximity sensor, an inductive sensor, an Eddy-current sensor, a passive infrared proximity sensor, a radar, a capacitive displacement sensor, a hall-effect sensor, a magnetic sensor, a GPS sensor, a thermal imaging sensor, a thermocouple, a thermistor, a photoelectric sensor, an ultrasonic sensor, an infrared laser sensor, an inertial motion sensor, a MEMS internal motion sensor, an ultrasonic 3D motion sensor, an accelerometer, an inclinometer, a force sensor, a piezoelectric sensor, a rotary encoder, a linear encoder, a chemical sensor, an ozone sensor, a smoke sensor, a heat sensor, a magnetometer, a carbon dioxide detector, a carbon monoxide detector, an oxygen sensor, a glucose sensor, a smoke detector, a metal detector, a rain sensor, an altimeter, an activity sensor, an object detector, a marker detector, a laser rangefinder, a sonar, a capacitive sensor, a heart rate sensor, and an RF/micropower impulse radio (MIR) sensor. The example sensors 228 of FIG. 2A include an IMU sensor(s) 228a and a gaze tracker 228b. The sensor(s) 228 may, for example, be operable to track head movement and pose (by the IMU sensor(s) 228a) and eye movement and position (by gaze tracking devices) of the weld operator wearing the head mounted system 20. The example gaze tracker 228b includes a light emitter (e.g., one or more infrared (IR) LEDs), a receptor (e.g., an image sensor) and electronics and software for data processing. The gaze tracker 228b may employ LED light to illuminate eye and sensor to detect light reflection off the cornea of each eye pupil. The gaze tracker 228b may include an inward-facing camera to capture eye position and movement frame by frame and/or special-purpose contact lenses having an embedded mirror and/or magnetic sensors. In addition to gaze tracking, the software may incorporate input from the IMU sensor(s) 228a for head movement together with input from pupil sensors to achieve better precision on the location of the physical scene observed by wearer's eyes. The combination of inputs from the IMU sensor(s) 228a and the gaze tracker 228b improves the computed accuracy of locations of virtual objects in the display so that the virtual objects relate to the directly observed physical objects in a mixed media environment. For example, when the head moves, or when the eye pupil moves, the virtual objects are re-rendered and repositioned in the display so that the relationship of the virtual objects and physical objects are kept. Example gaze trackers and methods of gaze tracking that may be used to implement the gaze tracker 228b and augmented reality controller 210 of FIG. 2A are described in U.S. Pat. No. 9,244,539, issued on Jan. 26, 2016. The entirety of U.S. Pat. No. 9,244,539 is incorporated herein by reference.

The example communications controller 230 disable a welding torch in response to the augmented reality controller 210 identifying a deviation from the weld instructions. For example, if the augmented reality controller 210 generates a simulated object for display that indicates a next weld to be performed at a first location in the weld environment, and detects (via the sensors 228 and/or the camera(s) 216) that the weld operator is directing the torch toward a different location, the example augmented reality controller 210 may signal the communications controller 230 to disable the torch. In response, the communications controller 230 generates the appropriate commands to disable the torch and transmits the commands via the communications interface 206 (e.g., to a power supply for the torch). In some examples, the communications controller 230 serves as an interface mechanism to the power supply and does not directly control the torch. The commands are received at and implemented by the power supply for the torch to disable the torch.

In some examples, the circuitry depicted as part of the head mounted system 20 may reside in any combination of the head mounted system 20, the equipment 12, the computer 30, and/or any other devices electrically and/or communicatively coupled to the head mounted system 20. For example, the GPU 218, or portions thereof, may reside in the computer 30 or equipment 12 where additional supply power may be available such that the GPU 218 can perform more intensive processing without draining the battery of the OHMD too quickly.

Figure 2B:
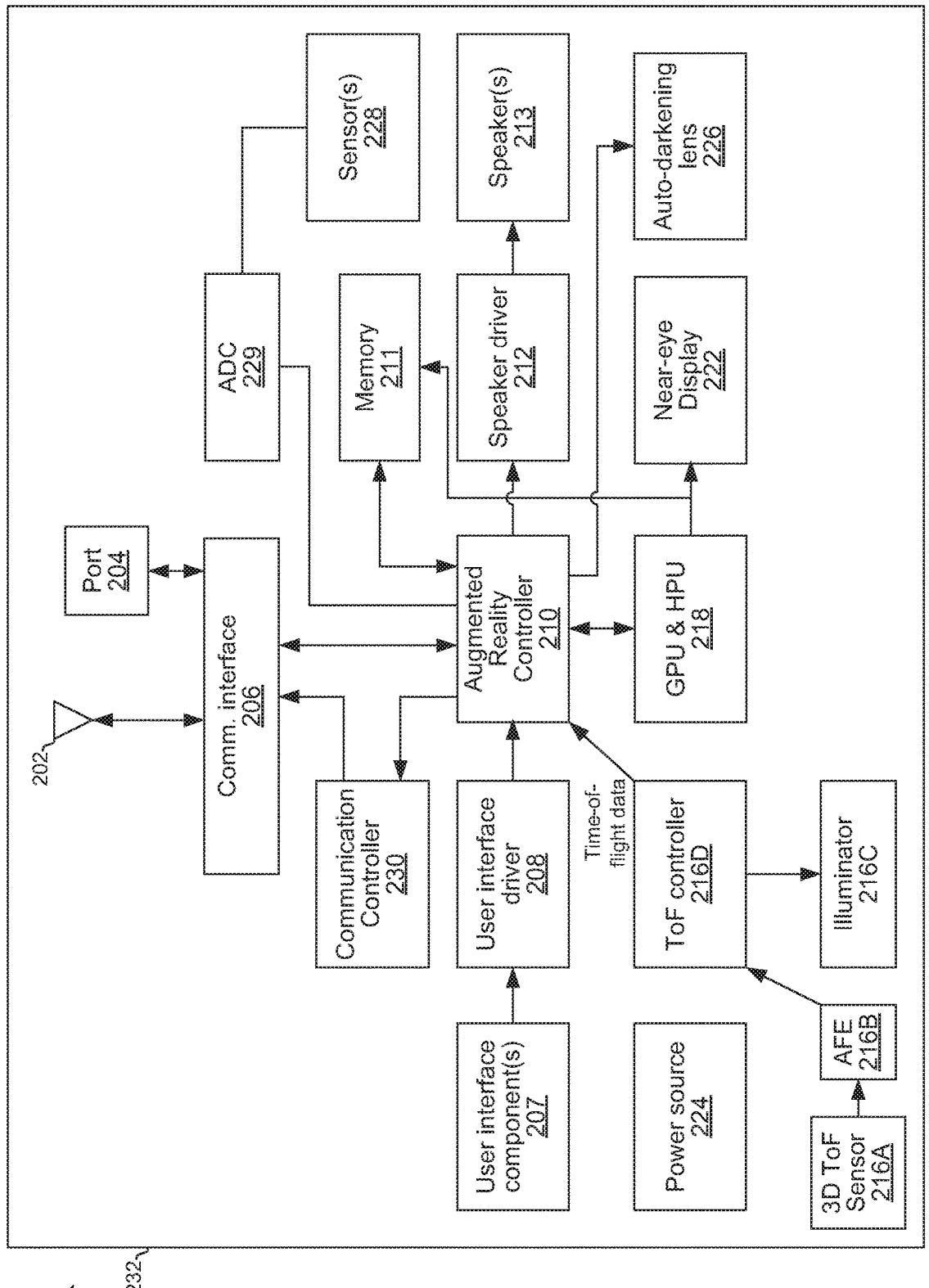

FIG. 2B is an example circuitry of the OHMD using ToF camera for welding of FIG. 1 detailing the drive circuit of ToF. ToF controller circuitry 216D controls the light pulse illuminator 216C, and the 3D ToF sensor or CMOS pixel array 216A via analog front end 216B. The ToF controller circuitry 216D may be, for example, a state machine that synchronizes the operation of 216A, 216B and 216C. The controller circuitry 216D may control the pixels scan, compute the depth measurement of each pixel, and performs de-aliasing, de-noising, frequency tuning and temperature compensation. The 3D ToF sensor 216A may be, for example, an addressable CMOS pixel array, with each pixel material tuned to respond to a specific optical wavelength, for example 850 nm-870 nm to match a 850 nm illumination light source (e.g., the illuminator 216C). The example illuminator 216C outputs the light (radiation) at a wavelength that is different than the arc light wavelength. The analog front end (AFE) 216B can be an array of sample-and-hold and high speed analog-to-digital converters (ADCs) for analog to digital conversion and serialization of the data. The controller 216D may acquire the serialized depth data from AFE 216B into a collection of 3D points, each point called a voxel, forming a depth map. Tof controller 216D may render the depth map into a 3D space called a point cloud and may convert the point cloud into mesh models through a process called surface reconstruction. ToF controller 216D may transmit the mesh model or point cloud to augmented reality controller 210. The example TOF sensor 216A includes a filter (e.g., a bandpass filter) that permits the wavelength(s) corresponding to the illuminator output and mitigates radiation at the arc light wavelength(s).

The example head mounted system 20 updates the image(s) presented on the near-eye display 222 as the wearer of the head mounted system 20 moves or changes perspective. For example, the optical sensor (e.g., the camera(s) 216, the ToF controller 216D) may collect additional images of the weld environment, which are used by the augmented reality controller 210 to update the position and the perspective of the simulated object(s). The graphics processor 218 and/or holographic processor 218 then updates the simulated images (e.g., the views of the simulated objects within the field of view) based on the updates to the position and/or the orientation by the augmented reality controller 210, and the near-eye display 222 displays the updated images to create the effect of augmented reality (e.g., the context-aware and/or perception-aware rendering, and/or placement and/or overlay of the simulated objects onto the environment).

In some examples, the communications interface 206 receives one or more weld parameters, such as travel speed, torch and travel angles, weld penetration, weld width, bead shape, arc length, heat input, that the operator of the torch is required to achieve during the weld. The example augmented reality controller 210 may receive actual weld process signals and/or feedback and present the signals to the operator via the near-eye display 222 with the simulated objects. In some examples, the augmented reality controller 210 compares the commanded parameters and actual feedback and process signals (e.g., a range of values for a commanded parameter, such as a range of arc lengths, heat input, metal deposition, etc.), and present the actual weld process signals compared to the commanded parameters. For example, the augmented reality controller 210 may generate a status bar representing acceptable and/or unacceptable ranges for a parameter, and include an indicator representing the current status of the parameter within the status bar.

In FIG. 2B, analog output signal(s) from the sensor(s) 228 are converted to digital signals by an analog-to-digital converter (ADC) 229. The digital signals may then be processed by the augmented reality controller 210. The ADC 229 may be included in other examples, and/or additional ADCs may be used by the example head mounted system 20.

Figure 2C:
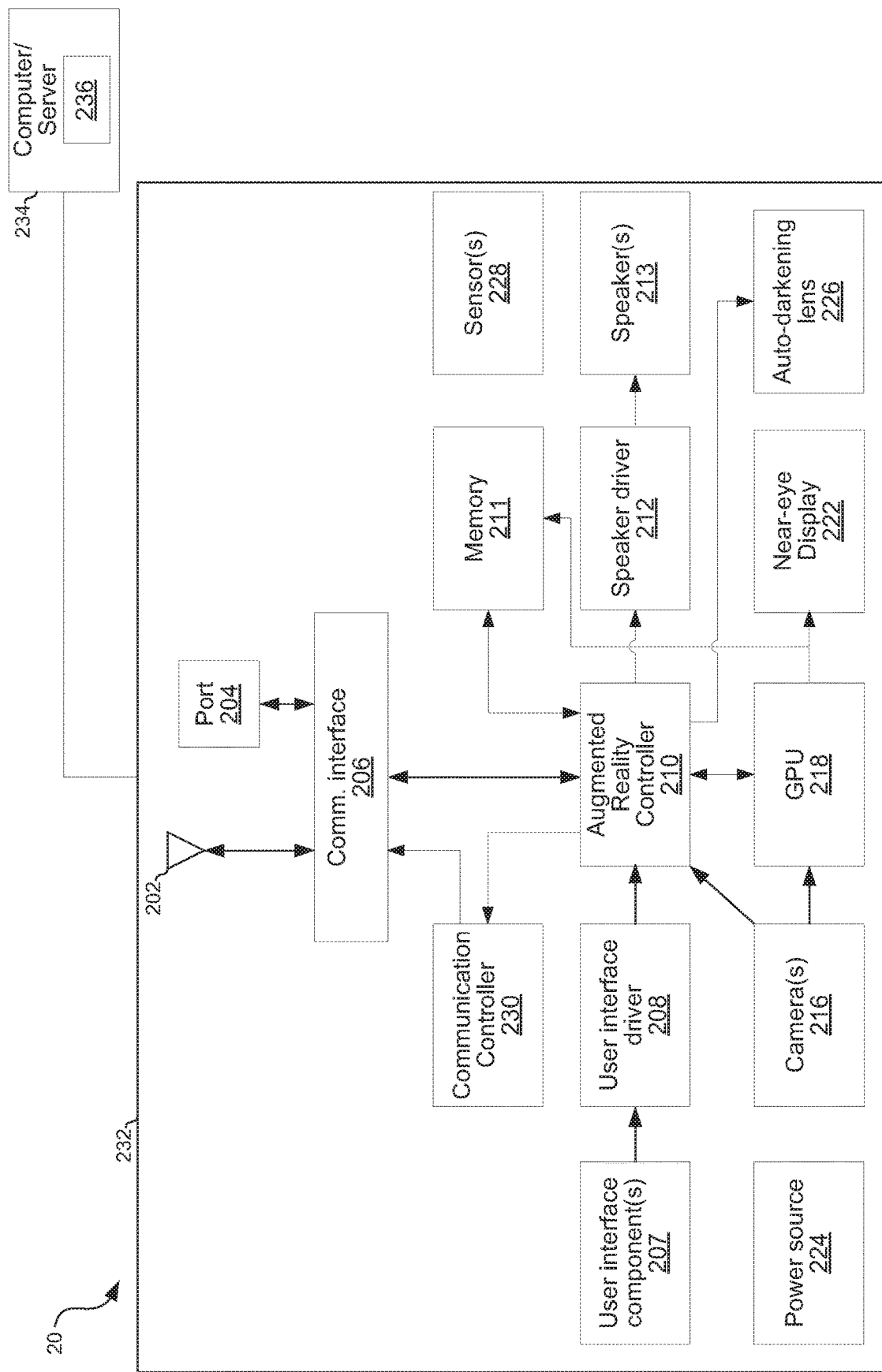

FIG. 2C illustrates another example implementation of the head mounted system 20 of FIG. 1. In some examples, all or part of the augmented reality calculations may be implemented by a computing device 234 or server in communication with the head mounted system 20 via the communications interface 206. The example head mounted system 20 may communicate with the computing device 234 via a dedicated wired or wireless connection, a communications network, and/or any other method of communication. In some examples, the communications between the head mounted system 20 and the computing device 234 mandate a minimum bandwidth and/or a maximum latency.

In such examples, sensor and/or image data collected at the head mounted system 20 are transmitted by the augmented reality controller 210 to a second (e.g., more powerful) augmented reality controller 236 in the external computing device 234. The augmented reality controller 236 may perform the generation and/or rendering of virtual objects (e.g., positioning and/or orientation) and return the virtual object information to the augmented reality controller 210 for final rendering and display via the GPU 218 and the near-eye display 222. In the example of FIG. 2C, the augmented reality controller 210 may perform tasks related to collection and transmission of images and/or sensor data.

While example implementations of the headwear 20 are described with reference to FIGS. 2A, 2B, and/or 2C, other implementations may be used. For example, any of the example antenna 202, the example port 204, the example communications interface 206, the example user interface components 207, the example user interface driver 208, the example augmented reality controller 210, the example memory 211, the example speaker driver 212, the example speaker(s) 213, the example camera(s) 216, the example GPU 218, the example near-eye display 222, the example power source 224, the example lens 226, the example sensor(s) 228, the example communications controller 230 may be implemented using hardware, software, firmware, and/or any combination of hardware, software, and/or firmware. For example, the example antenna 202, the example port 204, the example communications interface 206, the example user interface components 207, the example user interface driver 208, the example augmented reality controller 210, the example memory 211, the example speaker driver 212, the example speaker(s) 213, the example camera(s) 216, the example GPU 218, the example near-eye display 222, the example power source 224, the example lens 226, the example sensor(s) 228, the example communications controller 230 may be implemented using one or more integrated circuits and/or discrete circuits, such as general purpose processors, special purpose processors (e.g., digital signal processors), programmable logic devices. Furthermore, implementations may include combinations of components and/or functions into single integrated circuit packages and/or divisions of components and/or functions into multiple integrated circuit packages.

Figure 3:
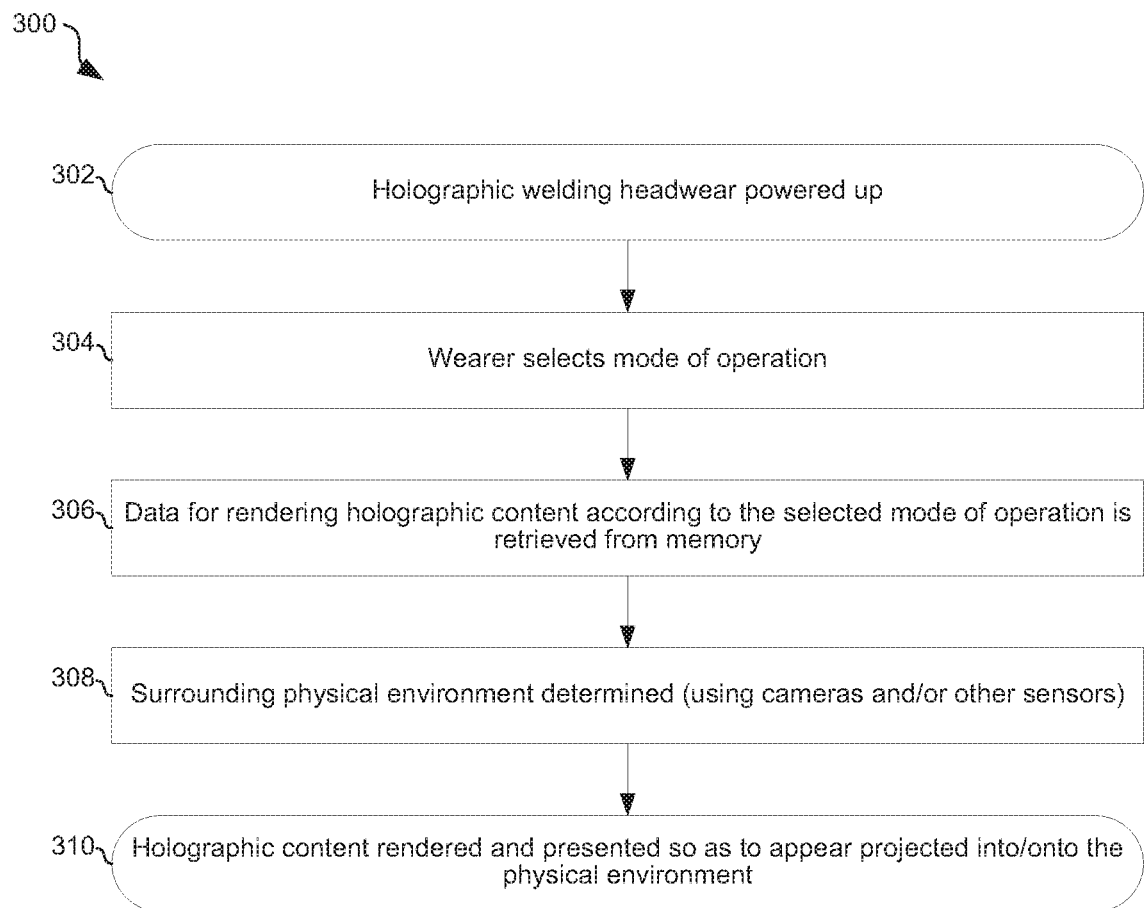
FIG. 3 is a flowchart representative of example machine readable instructions which may be executed by one or more processors to implement the OHMD of FIGS. 1, 2A, and/or 2B for welding.

FIG. 3 is a flowchart representative of example machine readable instructions 300 which may be executed by one or more processors to implement the head mounted system 20 of FIGS. 1, 2A, and/or 2B. The instructions 300 begin in block 302 in which wearer 108 puts on the augmented reality welding head mounted system 20 and powers it up.

In block 304, the wearer 108 selects a mode of operation of the head mounted system 20. For example, a menu may be projected by the head mounted system 20 in front of the operator to select or enter an operator identifier, job identifier, a WPS, a weld process, and/or to specify (e.g., via virtual manipulation of a virtual control via gesture control or touching virtual buttons or knobs projected and/or downloading from a network-accessible database) an arc length, heat input, deposition and/or weld size requirement. For example, there may be a pre-weld mode of operation in which the head mounted system 20 provides augmented reality instructions for a weld to be performed and preparation steps and checklist prior to welding, an in-weld mode of operation in which the head mounted system 20 provides augmented reality guidance for the weld operator during the actual weld, and a post-weld mode of operation in which the head mounted system 20 provides an augmented reality interface for inspecting a completed weld operation and other post-weld operational guidance.

In block 306, data for rendering holographic content according to the selected mode of operation is retrieved from memory. This data may include, for example, 3D CAD models or files or descriptions for rendering holographic objects such as the torch 104 and the objects 114; files containing previously-captured images of a completed weld operation which may be rendered for holographic viewing, computer-aided design files; files containing data captured (e.g., weld torch parameters, weld equipment outputs/settings, etc.) during a previous welding operation; and/or the like.

In block 308, the physical environment surrounding the head mounted system 20 is determined from images captured by the camera(s) 216 and/or from data collected by the sensor(s) 228. This may comprise, for example, determining a location of the workpiece 102 and/or torch 112 relative to the field of view of the wearer 108.

In block 310, the data retrieved in block 306 and the information about the physical environment determined in block 308 may be used for rendering 3D holographic content and presenting the content along with the physical environment (e.g., overlaid on a direct/passive view in an "augmented reality" system).

Figure 4A:
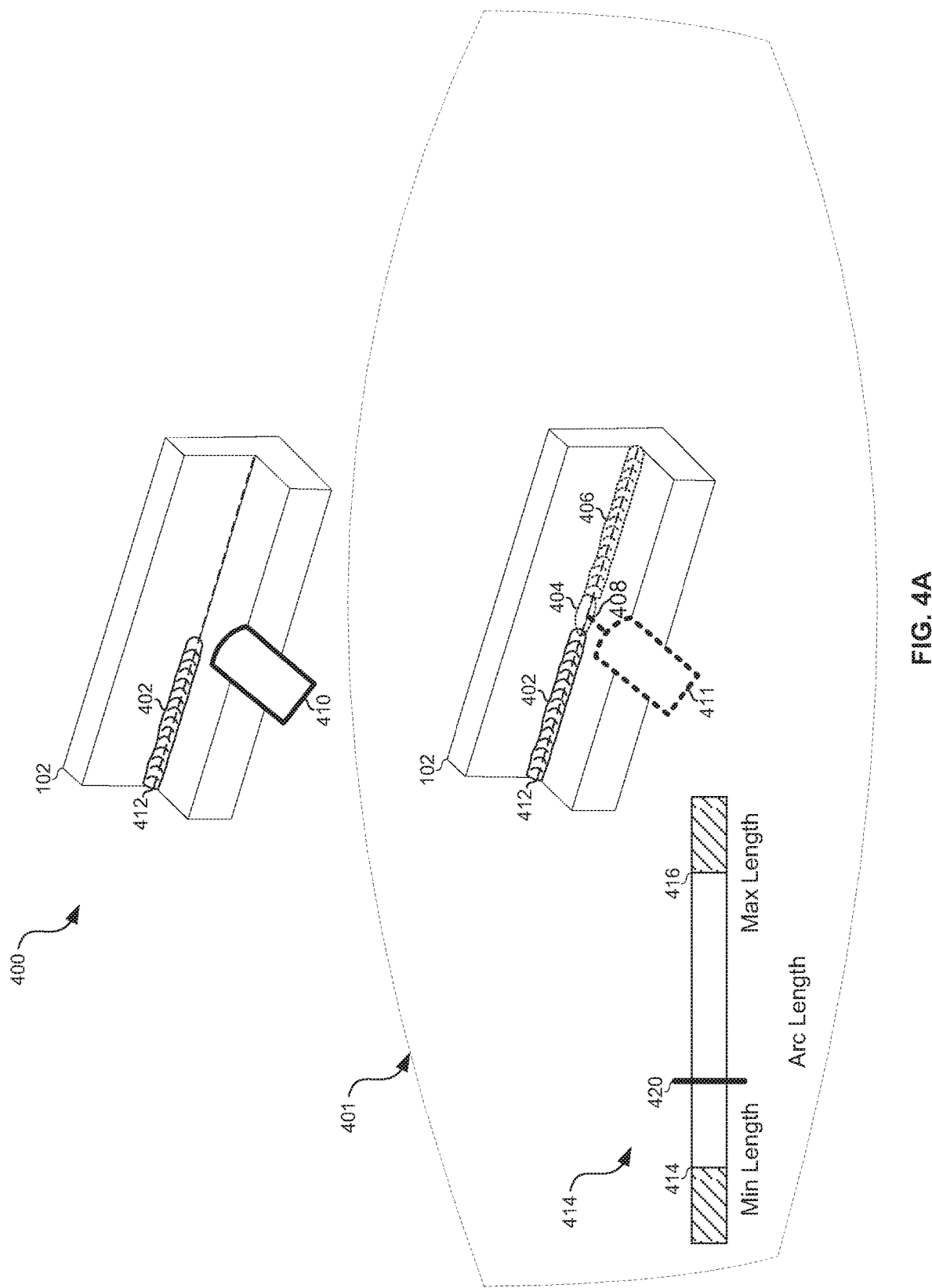
FIG. 4A depicts an example view through an augmented reality welding user interface during a welding operation.

FIG. 4A depicts an example view through an augmented reality welding user interface 401 during a welding operation in a weld environment 400. Shown in FIG. 4A is the actual workpiece 102 with example holographic objects rendered with their positions anchored to, or a set relative to, the workpiece 102. Objects shown in FIG. 4A include completed weld bead 402, weld puddle 404, future weld bead 406, wire stick out 408, torch 410, and seam 412.

Each of the completed weld bead 402, the weld puddle 404, the wire stick out 408, the torch 410, and the seam 412 may be the physical object or a holographic rendering of the object based on tracked object positions, head movement, CAD model, WPS, sensor data, etc. For example, the physical torch 410 is in the physical environment, and a holographic rendering 411 of the torch is overlaid in the user interface 401. Any particular object may be fully or partially represented by a holographic rendering when, or in areas of the view where, fume, spatter, arc glare, and/or other obstructions prevent the weld operator from seeing the actual object (or portions thereof). The rendering of the holographic versions of physical objects which are obscured may comprise using known information about the obscured scene to predict (with some probability) the current location of the object. In this manner, holographic images "reveal" the physical objects as if view of it/them by the operator was not obstructed.

The future weld bead 406 may be a holographic rendering showing a predicted finished weld bead (e.g., based on tracked current position, angle, movement, etc.) and/or a desired weld bead (i.e., an weld bead that would be laid down if all pertinent parameters and settings were maintained within tolerances throughout the duration of the weld operation. If the weld puddle 404 (actual or holographic/predicted) is misaligned with future weld position, or has a different size and/or location than the future desired weld, it is a cue to the weld operator to change his/her wire aiming or change his/her welding speed to match with the desired outcome of the future weld size. In one example, a virtual weld pool representing desired weld size in WPS (or set-point) can be projected onto the actual physical weld pool. The virtual weld pool may be larger or smaller than the physical weld pool which provides a clue for operator to speed up or slow down so that the actual physical weld pool size matches that of the virtual weld pool. In another example, if the augmented reality controller 210 detects a sufficiently large gap ahead of the physical weld puddle 404 by analyzing first image obtained from camera 216, the augmented reality controller 210 renders a zigzag symbol via the GPU 218 and projects the symbol via the near-eye display just ahead of the physical weld puddle 404 to prompt the operator to weave the torch, bridge the gap and prevent a burn-through defect. In some instances, text or symbols are annotated to the real scene for instructing the operator to change welding parameters (e.g., contact-tip-to-work distance, travel speed, torch angle and the like). Audio instruction can also be given thru the head mounted system 20. In an example implementation, tolerance thresholds can be pre-set so that if actual or predicted locations of objects of an observed scene depart from a model, a visual or audio alarm can be sounded. Additionally, or alternatively, the future weld bead 406 may be a holographic rendering showing a desired finished weld bead. That is, a weld bead that would be laid down if all pertinent parameters and settings were maintained within tolerances throughout the duration of the weld operation. This may serve as a guide for the operator as s/he performs the weld.

The example augmented reality welding user interface of FIG. 4A also includes a parameter status bar 414 that presents an actual weld process signal to the operator during the weld. The example status bar 414 includes a lower parameter limit 416, an upper parameter limit 418, and a current parameter status indicator 420. The example head mounted system 20 of FIG. 2A and/or 2B updates the parameter status bar 414 as the measured parameter changes, and updates the location of the status indicator 420 on the status bar 414.

Known information used for modeling/predicting the location of obscured objects may include, for example: last seen location and velocity of the various physical objects in the field of view (e.g., workpiece, seam, torch, electrode, weld puddle, etc., mechanical/CAD model for the various physical objects in the field of view, chemical and other materials data for the various physical objects, welding equipment settings and/or output (e.g., voltage, current, gas speed, and the like). Predicting location of the physical objects may also comprise modeling/predicting locations of obstructions such as fume, spatter, arc brightness, etc.

In addition to resolving obscured objects, a priori knowledge of a welding operation, a welding environment, welding equipment, weld operator, etc. may aid "scene understanding" in general. Such knowledge may include a model-based definition (MBD) and actual dimensions of other components to be fitted with the weldment or finished assembly with GD&T information, and to adaptively and dynamically adjust commanded weld parameters and tolerance windows of the weld parameters based on the specific weldment being welded. Together with camera images, the system can have a more holistic scene analysis based on a priori knowledge. For example, probabilistic graphic models (PGMs) can be used to decipher the objects and their behavior in the scene, rather than relying on the images or videos alone. For example, the system may be configured to recognize that light streaks originating from the arc below the end of the welding wire and scattering at high speed outward are likely to be spatter balls. As another example, the system may have information as to the presence (and possibly location) of tack welds that exist in the joint and may take this information into account in its seam tracking algorithms. As yet another example, the system may be configured with predetermined limits on physical capabilities and/or parameters (e.g., in practice the torch cannot be physically traveling above a certain speed, etc.). As yet another example, the system may store acoustic characteristics associated with various welding processes/parameters (e.g., a long arc may emit sound having a first set of frequencies, amplitudes, etc.; a short arc may emit sound having a second set of frequencies, amplitudes, etc.; and an ideal arc may emit sound having a third set of frequencies, amplitudes, etc.). Such multi-dimensional multi-variable a priori knowledge collectively may be used for image segmentation, 3D object reconstruction, and scene interpretation. PGMs may employ methods like Bayesian networks and Markov random fields, or discrete data structures to encode and manipulate probability distributions in multi-dimensional spaces.

Figure 4B:
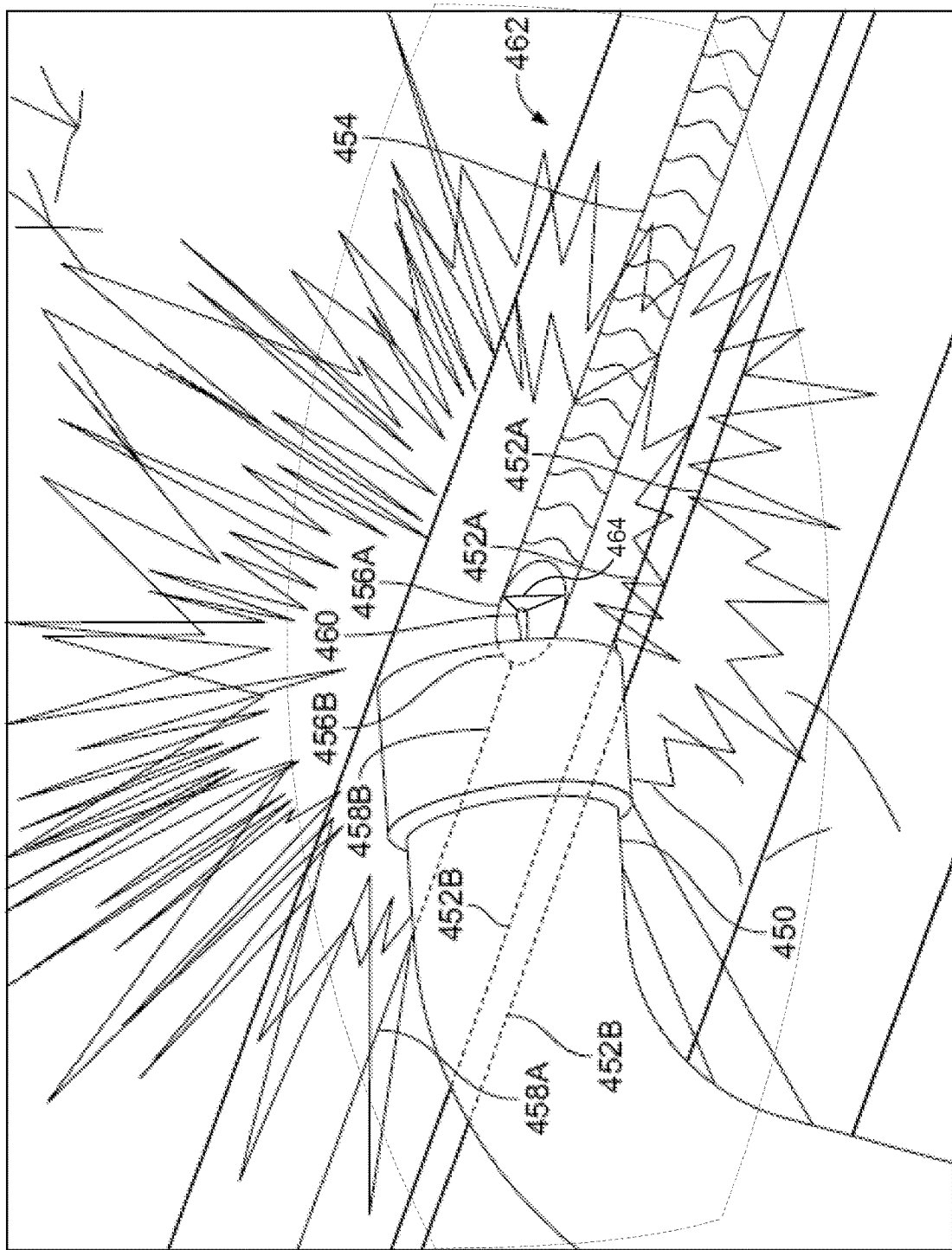
FIG. 4B depicts another example view through an augmented reality welding user interface during a welding operation.

FIG. 4B depicts another example view through an augmented reality welding user interface during a welding operation. The view is a mix of real welding scene and a 3D virtual objects or holograms superimposed onto the real scene. In the example shown, the 3D virtual objects are "outlines" or wire-frame models of real objects, in other words, unfilled or transparent 3D models of the real objects. Specifically, shown is a virtual outline or wire-frame model of torch 450, workpiece 462, weld bead 454, weld puddle 456, and seam 458, where the dotted lines in the hologram represent virtual objects (or portions of objects) that are physically blocked in the real scene but viewable from the virtual scene. For example, a portion 456B of the weld puddle is physically blocked from view by the real torch and therefore represented with dotted lines while a portion 456A of the puddle is in the operator's line of sight and thus represented with solid lines. Similarly, a portion 458B of the seam is physically blocked from view by the real torch and therefore represented with dotted lines while a portion 458A of the puddle is in the operator's line of sight and thus represented with solid lines. Likewise, a portion 452B of the edge of the workpiece 462 is physically blocked from view and therefore represented with dotted lines while a portion 452A of the puddle is in the operator's line of sight and thus represented with solid lines. In the same manner, a visible portion of the wire 460 may be represented with a solid line and the obscured portion of the wire with a dotted line. Although solid and dotted lines are used for contrasting objects in view and objects the view of which is obstructed, this may be accomplished in other ways (e.g., different line thickness, color, static vs flashing lines, etc.). A benefit of this is that the viewer/operator can see thru the fume, spatter, and physical objects obstructions and see the weld scene much better. Alternatively, only obscured scene (dotted) may be shown, while solid lines of observable objects are not annotated in the hologram.

Referring to FIG. 4B again, one embodiment is to train operator to practice welding using a real welding torch, a real workpiece, a real weld fixture and a real welding power supply, but without a real weld arc. Instead, the head mounted system 20 displays to the operator a simulated arc, a simulated weld pool, and a simulated weld overlaid onto the real workpiece in front of the operator. In other words, the torch 450, the wire 460, the workpiece 462, and the seam 458A are all real, but the weld puddle 456 and the weld arc are virtual or simulated (a virtual arc is not illustrated in FIG. 4B). In some such example training operations, the operator can configure the welding equipment (e.g., the power source for the welding current) as if the operator is about to perform a real weld, while the welding equipment operates in a simulation mode. The welding parameters from the equipment are received at the augmented reality controller 210 to provide information about how to render the virtual arc and the weld based on the selected welding parameters. When the trigger is pulled on the torch by the operator, instead of turning on the power supply output and feeding wire, the trigger sends an augmented reality (AR) arc start signal to the augmented reality controller 210 via the communications interface 206 and the port 204.

In response to receiving the augmented reality arc start signal, the augmented reality controller 210 renders the virtual arc, the virtual weld puddle 456 and virtual weld bead 454) and projects them to the near-eye display 222 so that the virtual objects blend into the real scene to create a visual illusion or simulation of live arc welding. However, there is no actual arc, no weld puddle and no wire feeding in the actual scene.

The example speaker(s) 213 output an arc sound that synthesizes a binaural sound effect to simulate the sound originating from the location of the virtual arc in the scene. The tones output by the speaker(s) 213 change based on the selected welding process, selected shielding gas, the arc length, and/or the voltage settings programmed on the welding power supply (short circuit, pulse, CV etc.). When the operator changes contact tip to work distance, torch angles, and/or travel speed, the augmented reality controller 210 adjusts the virtual objects and the binaural sound accordingly based on the "first image" or depth map measurement and/or the interpretation of the welding scene by the augmented reality controller 210. Likewise, if the operator changes the machine settings on the welding equipment on the fly, the augmented reality controller 210 adjusts the rendered virtual objects and/or the binaural sound. In response to release of the trigger by the weld operator, the welding equipment sends an AR arc stop signal to the augmented reality controller 210. In response to the arc stop signal, the augmented reality controller 210 updates the virtual objects to removes the arc object and the puddle object 456, but retain the weld bead object 454, in the hologram displayed on the near-eye display 222. In some examples, the augmented reality controller 210 generates a visual display of summary data of the virtual weld (e.g., overall heat input, average travel speed, weld score, etc.) for display via the near-eye display 222.

From the operator's/viewer's perspective, the virtual objects are spatially anchored (or "glued" or "pinned") to the locations and orientation of the real objects, regardless of viewer's head and/or eye movement or movement of the physical objects. Virtual object anchoring may be accomplished using a 3D depth ranging camera (e.g. ToF) for mapping out the scene of real objects and by using head tracking IMUs and/or gaze tracking devices to detect where and/or at what physical objects the viewer is looking at in the physical environment. The welding arc, however, presents significant challenges to accomplishing anchoring. For example, stereo vision with dual cameras capturing the visible spectrum may suffer from being blinded by the arc, thus obscuring the surrounding objects/portions of the scene. The ToF camera mapping overcomes this problem by illuminating the scene with a coherent laser of single wavelength away from arc spectrum peaks and capturing the reflected light with an imaging sensor with optical filter that receives only the laser wavelength and rejects the others, such as from the intense arc.

Referring to FIG. 4B again, in some examples, a virtual arc object 464 can be rendered and overlaid atop the physical arc object. The virtual arc object 464 can be rendered densely opaque and used to dim or block the physical arc object to improve visibility of the surrounding areas. The virtual arc object 464 blocking the actual arc may be repositioned to match with head and/or eye movement from IMU motion tracking/gaze tracking inputs. The display may comprise electrochromic material or suspended particle for the darkening effect. The opacity of the virtual arc object 464 may fade out beyond the edges of physical arc object to account for the inaccuracy of the arc object coordinates.

Figure 4C:
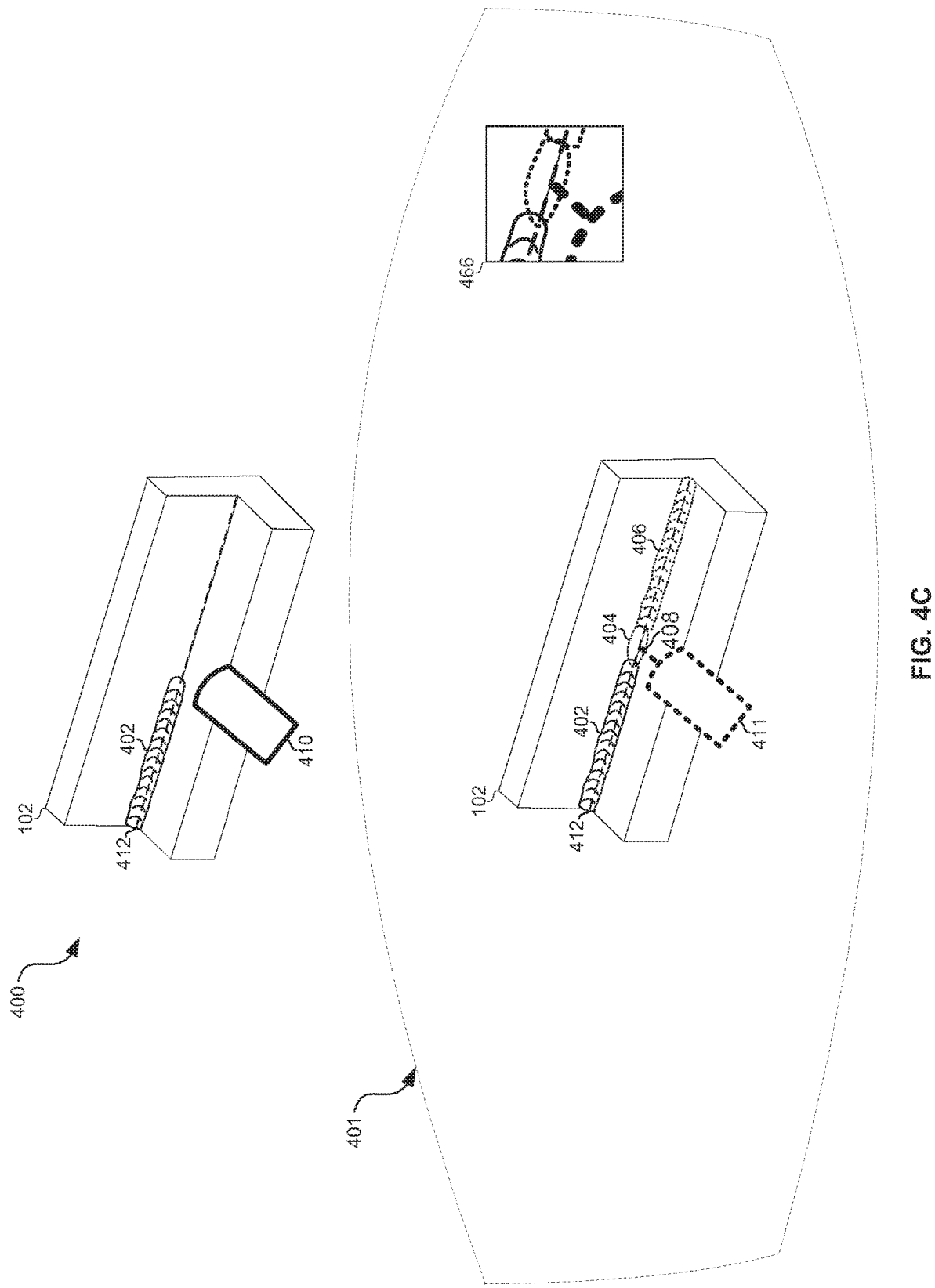
FIG. 4C illustrates another example user interface in which a gaze tracking device determines the physical object being gazed on or gaze location in the scene, and uses the determined location or object to provide a zoom view of the gazed area in the display.

Referring to FIG. 4C, in some examples, the gaze tracking device determines the physical object being gazed on or gaze location in the scene 400, and uses the determined location or object to provide a zoom view 466 of the gazed area in the display. As the viewer moves head/eye, the zoom target will also move automatically to match with the newly gazed area. The zoom view 466 is useful, for example, in delicate welding of small workpieces and/or in high precision applications. In some examples, the augmented reality controller 210 activates, deactivates, and/or repositions the zoom view 466 based on user inputs such as gesture recognition, head nodding or shaking, eyelid brink pattern, and/or voice recognition.

Referring to FIG. 4B again, in some examples, the gaze tracking device may provide insight of viewer's attention in welder training. Manual welding is all about hand-eye coordination. An experienced operator may selectively may attention to joint for seam tracking, to puddle for weld size and penetration, to wire relative to seam for wire placement, to weld toe for wetting, etc. Inexperienced operator or student operator may not be paying attention to the right place at the right time, and may suffer from a psychological effect called "inattentional blindness." Feedback on viewer's gaze may provide proxy of viewer's psychological blindness. In one example, when viewer is not looking at the object (e.g. weld toe) as asked by weld instructor, a virtual object or marker may annotate the desired object to draw viewer's attention or voice instructions may be provided to pay attention to the desired object. In another example, when viewer is not looking at the object (e.g. weld puddle) as the weld is getting too big, a virtual weld puddle of smaller size can be overlaid on the large physical puddle, and voice instruction can be given to the student to pick up some travel speed in moving the torch so that a smaller puddle/weld can be put down.

Figure 4D:
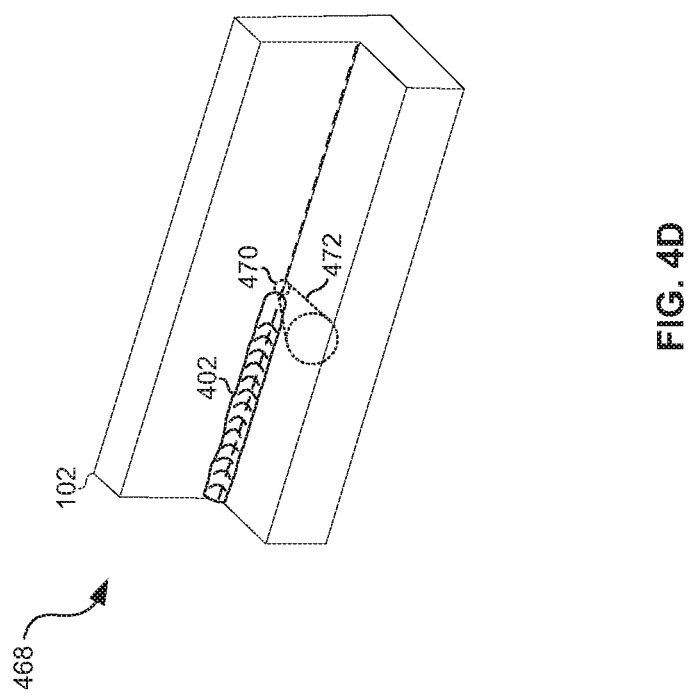
FIG. 4D illustrates another example user interface in which a simulated object (e.g., one or more lasers used in welding and/or cutting operations) are displayed on the head mounted display of FIGS. 2A, 2B, and/or 2C.

FIG. 4D illustrates another example user interface 468 in which a simulated object (e.g., one or more lasers used in welding and/or cutting operations) are displayed on the head mounted display of FIGS. 2A, 2B, and/or 2C.

In laser welding, laser-GMAW hybrid welding, laser cladding and laser cutting, knowledge of the laser focus position, the focal length, and/or the shape of laser envelope, relative to the part/weldment to be processed and/or in relation with powder/wire delivery in 3D additive manufacturing, cladding, or surfacing applications, may affect the quality of the resulting operation. Conventional systems use a low power visible laser to display an indicator for the purposes of alignment. However, the conventional alignment method may lack sufficient accuracy to indicate the focal point (e.g., due to a roughly fixed spot size of the alignment laser), the depth of focus, and/or the laser envelope.

The example head mounted systems 20 of FIGS. 2A-2C illustrate an example focal point 470 and an example laser envelope 472 as holographically-illustrated objects in the weld environment. The example interface 468 also illustrates the weld bead 402 and the workpiece 102. Additionally or alternatively, the focal point 470 and the laser envelope 472 can be displayed as a rendered 3D image on a computer monitor external to the head mounted system 20.

When the head mounted system 20 is used, the example head mounted system 20 may be provided with an eye protection lens that filters out the wavelength of the specific material processing laser (e.g., instead of an auto-darkening lens 226). The head mounted system 20 project virtual object(s) simulating the laser output, such as the focal point 470 and the laser envelope 472. The example virtual objects 470, 472 may assist the alignment of laser in programming a robot for welding, cladding, and/or cutting. The virtual objects 470, 472 provide a virtual laser image to illustrate the location of the laser during actual welding when the laser has invisible wavelength (e.g., from 800-1064 nanometers for solid state lasers or 10.6 micrometer for CO2 gas laser). The virtual objects 470, 472 may also illustrate the laser envelope and/or the gas envelope for a laser powder process or a wire deposition process.

Figure 5:
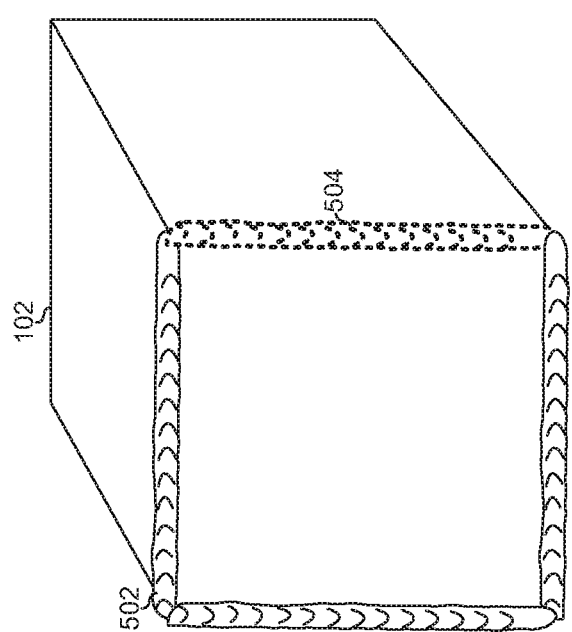
FIG. 5 depicts an example weld sequencing control view through an augmented reality welding user interface.

In some examples, the augmented reality controller 210 of FIGS. 2A and/or 2B determines a status of a weld being performed and compares the status to the weld instructions. For example, the augmented reality controller 210 may determine that an operator is performing a particular weld in a sequence of welds defined in the instruction. Based on the determined status, the augmented reality controller 210 determines the position and the perspective of the simulated object(s). FIG. 5 depicts an example weld sequencing control view through an augmented reality welding user interface. In FIG. 5, the workpiece is a box with 12 edge welds, which are to be welded in sequence to avoid distortion of the workpiece 102. As the welder completes weld 502, a blinking hologram of weld 504 (to be welded next) pinned or anchored to the workpiece 102 from the view of the human operator is displayed to alert the operator to move his body and his torch towards the weld 504 position. The speaker 213 may output spatial sound effects such as a sound prompt coming from the weld 504 to draw the operator's attention. In an example implementation, if the human welder takes actions which indicate s/he is attempting to perform an out-of-sequence weld, the head mounted system 20 may send a signal to disable the trigger of the torch (e.g., via the communications controller 230) so that human error of welding in the wrong sequence can be avoided. In some examples, the head mounted system 20 permits the operator to override the communications controller 230. The head mounted system 20 may require the operator to confirm that the override and the different weld sequence is intentional before re-enabling the trigger of the torch.

Figure 6:
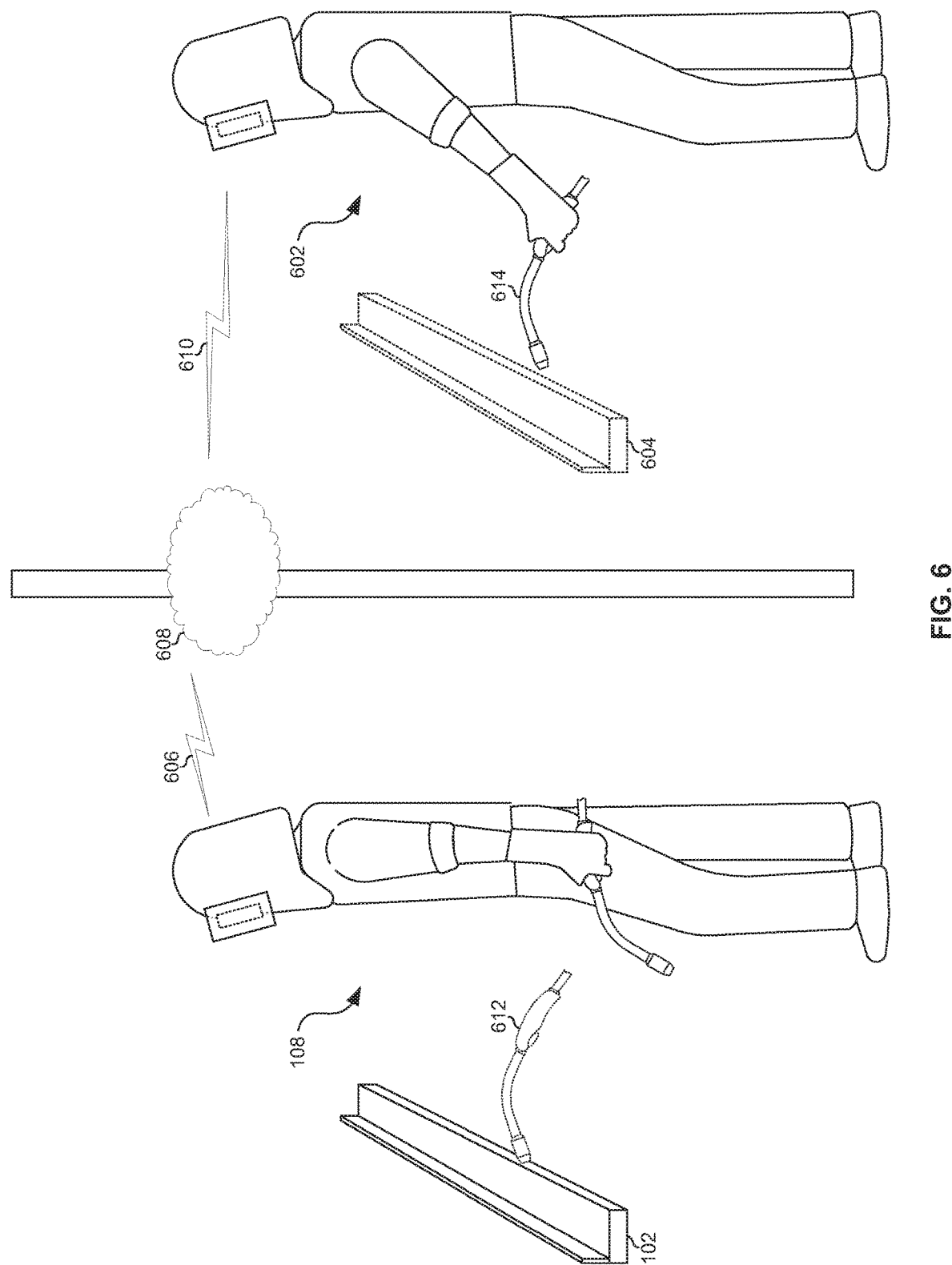
FIG. 6 depicts collaboration among disparately located weld operators using an augmented reality welding user interface.

FIG. 6 depicts collaboration among disparately located weld operators using an augmented reality welding user interface. In FIG. 6, the high field of view (FOV) depth camera in the head mounted system 20 relays (via connections 606 and 610 and network 608) the real images of the scene seen by operator 108 to a remote operator or instructor or service provider or supervisor 602, the "helper". The helper 602 may chat with the operator 108 to, for example, instruct the operator 108 on how to perform various welding tasks.

As an example, the helper 602 may see a holographic rendering 604 of the workpiece 102 seen by operator 108 and the operator 602 may see a holographic rendering 612 of a torch held by the helper 602. For example, to show the operator 108 how to hold the torch and weld the workpiece 102, the helper 602 may perform a simulated weld along the virtual workpiece 604 with the real torch 614. The virtual torch 612 may track the movements of the real torch 614. The operator 108 may thus see the virtual torch 612 performing the simulated weld along the real workpiece 102. As the helper 602 performs the simulated weld, a holographic bead may be projected onto the workpiece 102. Similarly, as the helper 602 performs the simulated weld, text and/or graphical annotations may be created (e.g., in response to commands entered by helper 602) and projected onto the view of operator 108.

In another example, operator 108 is having difficulty welding with arc burning back to a contact tip in the real torch in his/her hand (not labeled). The helper 602 may, for example, instruct the operator/user to replace a contact tip, and projecting the 3D drawing hologram of the contact tip onto the real scene of the torch the operator is holding. As another example, the operator 108 may report (speak into the microphone of his/her head mounted system 20) a porosity problem, and gesture to point to his gas delivery system. The helper will annotate (e.g., using gesture, voice, touch pad, keyboard, etc. the helper can cause the display of, and subsequent manipulation of, virtual objects that the operator sees) the real gas hose connections in the operator's real scene and voice the operator to check the gas hose for leak. Alternatively a 3D model hologram of the entire gas delivery with potential leak spots will be superimposed on the real scene along with pointers and text for operator to see and check.

In another example implementation, the remote helper 602 may not be wearing head mounted system 20 but may just see 2D images on a screen and may be enabled to control holographic images presented to the operator 108 using any suitable input device (gesture, voice, mouse, keyboard, voice, gestures, and/or the like). In another example implementation, the remote helper may not be a person, but instead may be a remote computer with high processing power, artificial intelligence, and/or the like.

Figure 7:
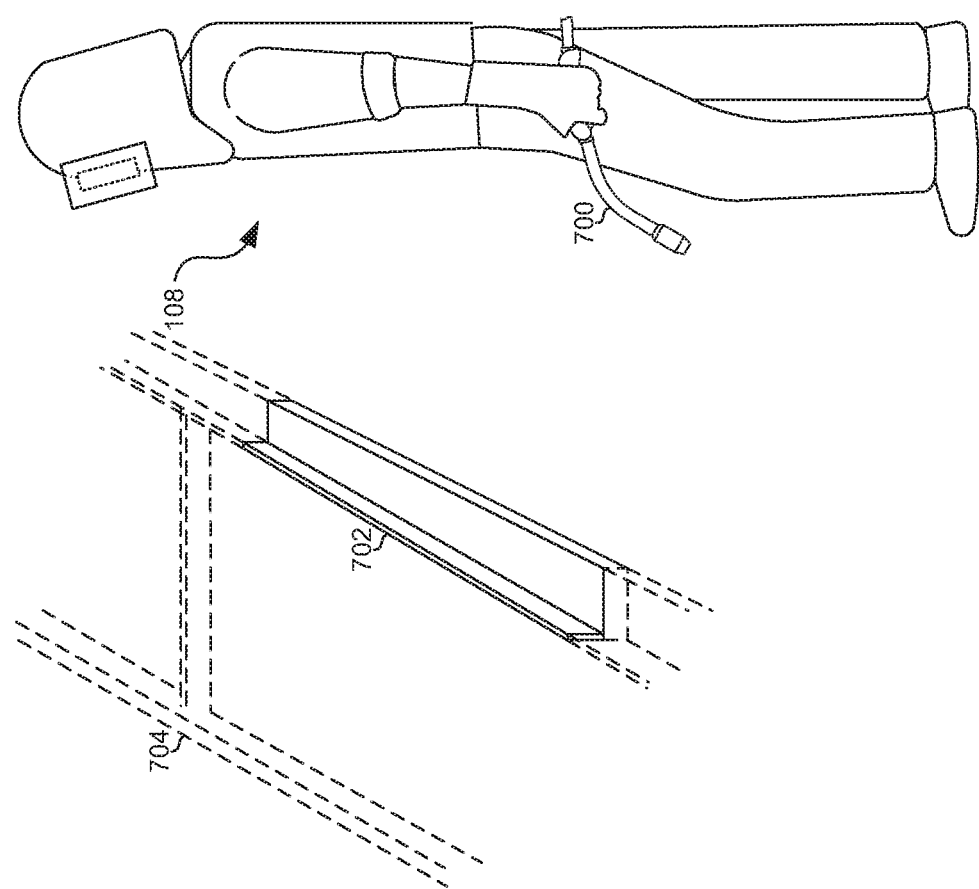
FIG. 7 illustrates use of an augmented reality user interface for improving the realism of a welding situation when practicing on a coupon.

FIG. 7 illustrates use of the example head mounted system 20 of FIGS. 2A and/or 2B to implement an augmented reality user interface for improving the realism of a welding situation when practicing on a coupon. In FIG. 7, the operator 108 is holding an operational torch 700 powered by an operational power source and wire feeder, in front of a test weld specimen 702 (also referred to as a test coupon). However, a hologram of 3D drawing/model of the actual weldment or finished assembly (e.g., a ship hull fragment) 704 is superimposed on the test coupon 702 and the operational gun torch 700 in a mixed reality. The superimposition of the hologram over the environment enables the operator to simulate welding in the future welding environment and actual weldment s/he is assigned to do while practicing on low cost coupons in a simulated environment. Use of the example augmented reality user interface of FIG. 7 enables an operator to become familiar with the task before s/he actually welds on a real structure, e.g. a ship, a car, a nuclear vessel, a jet engine. Such example simulations are valuable by reducing the risk of mistakes in weld situations that could be very expensive or impossible to correct and/or redo (e.g., expensive workpieces, workpieces that can only have one weld attempted, etc.). Examples of welding situations that are difficult to repair include repairing a large structure and/or welding on a very expensive material where scrap or failure is cost prohibitive.

Additionally or alternatively, the example head mounted system 20 of FIGS. 2A and/or 2B simulates the effect of any welding problems, such as simulating an abrupt gas cut-off during welding and replacing a view of an actual well (which may have been done properly with acceptable results) with a hologram of bad weld full of holes (because gas is missing). In other examples, the example head mounted system 20 of FIGS. 2A and/or 2B simulates physical obstructions that the operator will encounter when welding the actual weldment. For example, walls, blind spots, corners, etc. can be simulated. In the case of walls or other physical barriers, for example, the system can detect if a physical object (e.g. the torch, the hose, a part of the operator's body) intrudes into space which, in the real weldment, will be occupied by a physical structure and, if such is detected, trigger a warning, stop the simulation, and/or the like.

Figure 8:
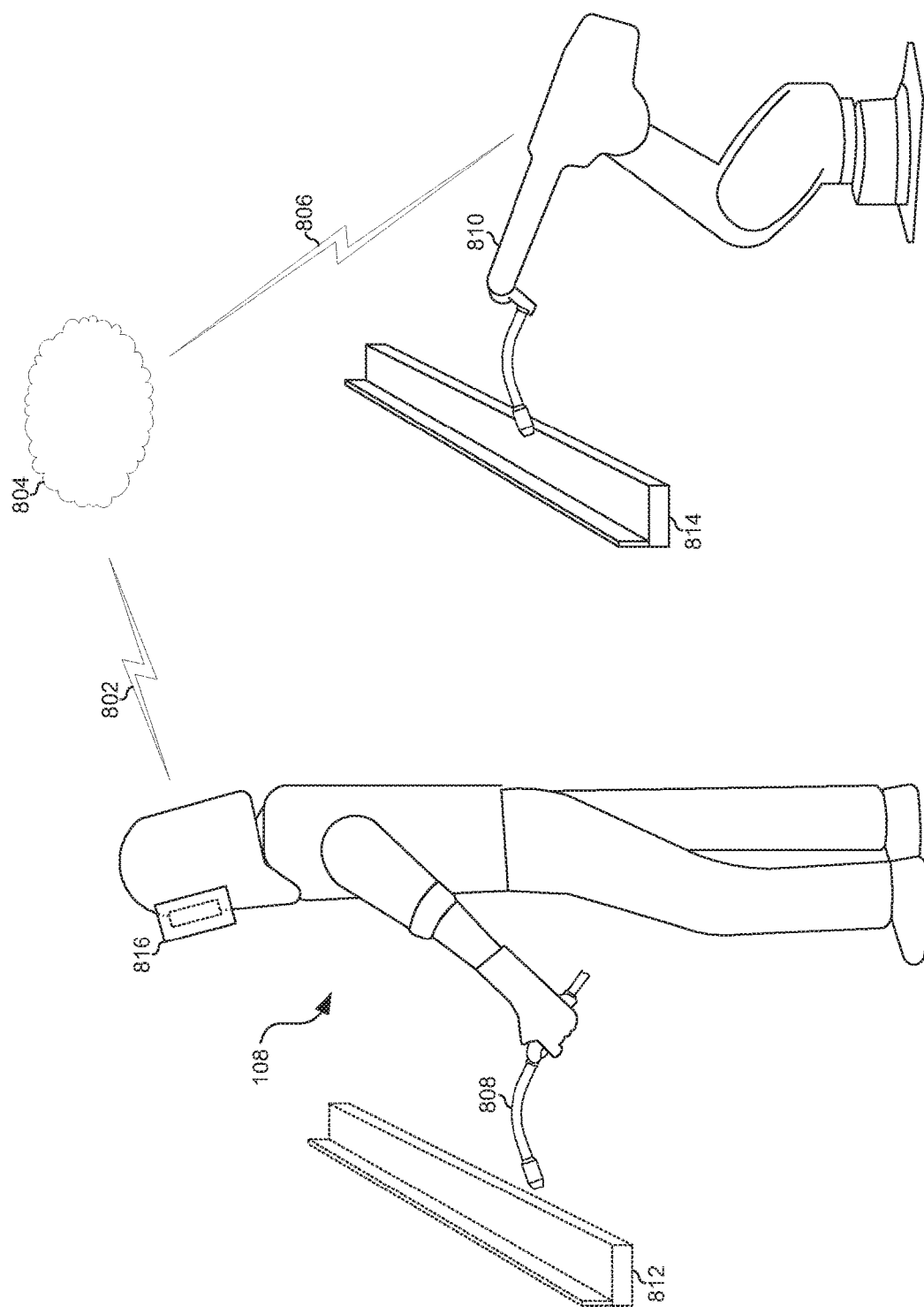
FIG. 8 illustrates control of welding robot using an augmented reality user interface.

FIG. 8 illustrates control of welding robot 810 using an augmented reality user interface. Cameras onboard the robot 810 capture 3D images of a workpiece 814 and relay the images to an OHMD 816 of the operator 108, which projects a holographic representation 812 of the workpiece 814. The example OHMD 816 of FIG. 8 may be implemented using the head mounted system 20 of FIGS. 2A and/or 2B. The human operator 108 holds a torch 808 and mimics performing a weld on the holographic workpiece 812. His torch positioning and movement is tracked by ToF camera and other sensors, and relayed to the robot 810 to perform the same weld robotically. In an example implementation, the robot follows the movements of the operator 108 in real-time. In another implementation, the human welder movement of the torch 808 may be recorded and transcribed to robot programming offline rather than in real time. This may be used, for example, where the robot is welding underwater, at high elevation, or in a hazardous environment (e.g. with radiation in a plutonium fueled reactor or on Mars). Thus, the robot 810 is an avatar of the human operator 108, where the robot 810 could be in a dangerous environment and the human operator 108 could be in the comfort of a lab.

Figure 9:
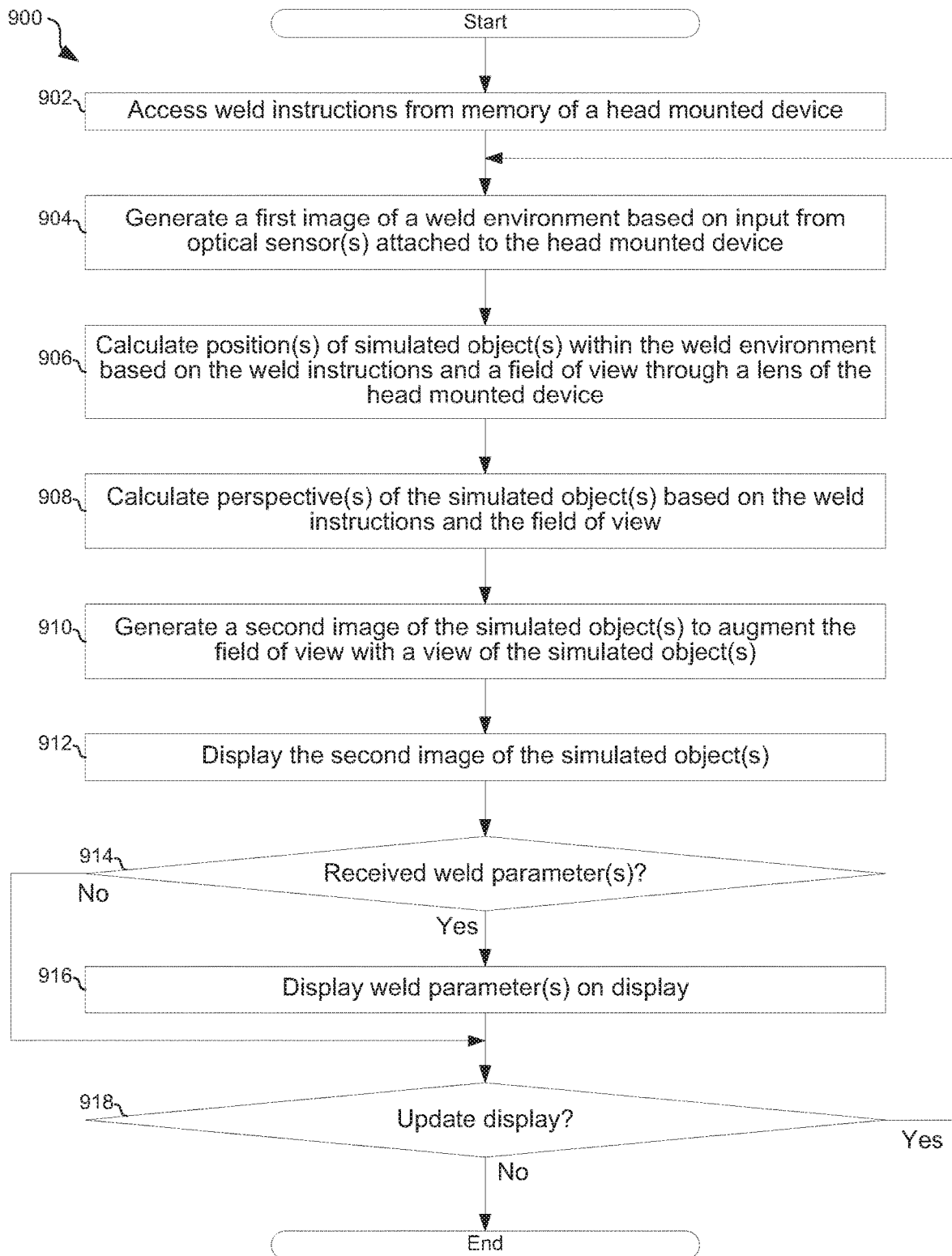
FIG. 9 is a flowchart representative of example machine readable instructions which may be executed by one or more processors to implement the OHMD of FIGS. 1, 2A, 2B, and/or 2C to augment a view of a weld environment.

FIG. 9 is a flowchart representative of example machine readable instructions 900 which may be executed by one or more processors to implement the system 20 of FIGS. 1, 2A, and/or 2B to augment a view of a weld environment. The example instructions 900 may be executed by the augmented reality controller 210 and/or the graphics processors 218 of FIG. 9 to implement a method or process to augment a view of a weld environment.

At block 902, the augmented reality controller 210 accesses weld instructions from the memory 211, where the weld instructions corresponding to a weld to be performed in a weld environment. For example, the weld instructions may be received and/or stored in the memory 211 prior to execution of the instructions 900.

At block 904, the augmented reality controller 210 generates a first image of the weld environment based on input from an optical sensor attached to a head mounted device. For example, the augmented reality controller 210 may receive image data from the camera(s) 216 and/or the ToF processor 216D of FIGS. 2A and/or 2B. In some examples, the input from the optical sensor is time-of-flight data, and the generating of the first image of the weld environment includes converting the time-of-flight data to the first image, performing segmentation, feature extraction, surface fitting, classification, object recognition, 3D scene reconstruction and/or dimensional measurement.

At block 906, the augmented reality controller 210 calculates position(s) of one or more simulated object(s) within the weld environment based on the weld instructions and a field of view through a lens (e.g., the auto-darkening lens 226) of the head mounted device.

At block 908, the augmented reality controller 210 calculates perspective(s) of the simulated object(s) based on the weld instructions and the field of view.

At block 910, the graphics processor 218 generates a second image of the simulated object(s) to augment the field of view with a view of the simulated object. For example, the graphics processor 218 generates the second image using the position(s) and the perspective(s) calculated by the augmented reality controller 210.

At block 912, the near-eye display 222 displays the second image of the simulated object(s). For example, the near-eye display 222 may display the simulated object(s) such that they occlude portions of the weld environment to give the operator the appearance that the simulated object(s) are present in the weld environment, while giving the operator the ability to view non-occluded parts of the weld environment.

At block 914, the augmented reality controller 210 determines whether any weld parameters have been received.

If one or more weld parameters have been received (block 914), at block 916 the near-eye display 222 displays the weld parameter(s). In some examples, the augmented reality controller 210 converts the weld parameters to a visual display, such as a visual comparison to a required range of weld parameters, and the visual display is presented via the near-eye display 222.

After displaying the weld parameters (block 916), or if no weld parameters were received (block 914), at block 918 the augmented reality controller 210 determines whether the display is to be updated with new position(s) and/or perspective(s) of the simulated object(s). If the display is to be updated (e.g., due to movement of the wearer of the head mounted display) (block 918), control returns to block 904) to generate another image. For example, the augmented reality controller 210 may generate a second image of the weld environment based on second input from the optical sensor 216, determine a change in the field of view, calculate second perspective(s) of the simulated object(s) within the weld environment based on the change in the field of view (where the position of the simulated object(s) within the weld environment may be constant and/or may be moved). The example graphics processor 218 may generate a third image of the simulated object(s) corresponding to the position(s) and the second perspective(s). The near-eye display 222 may display the second image of the simulated object.

Figure 10:
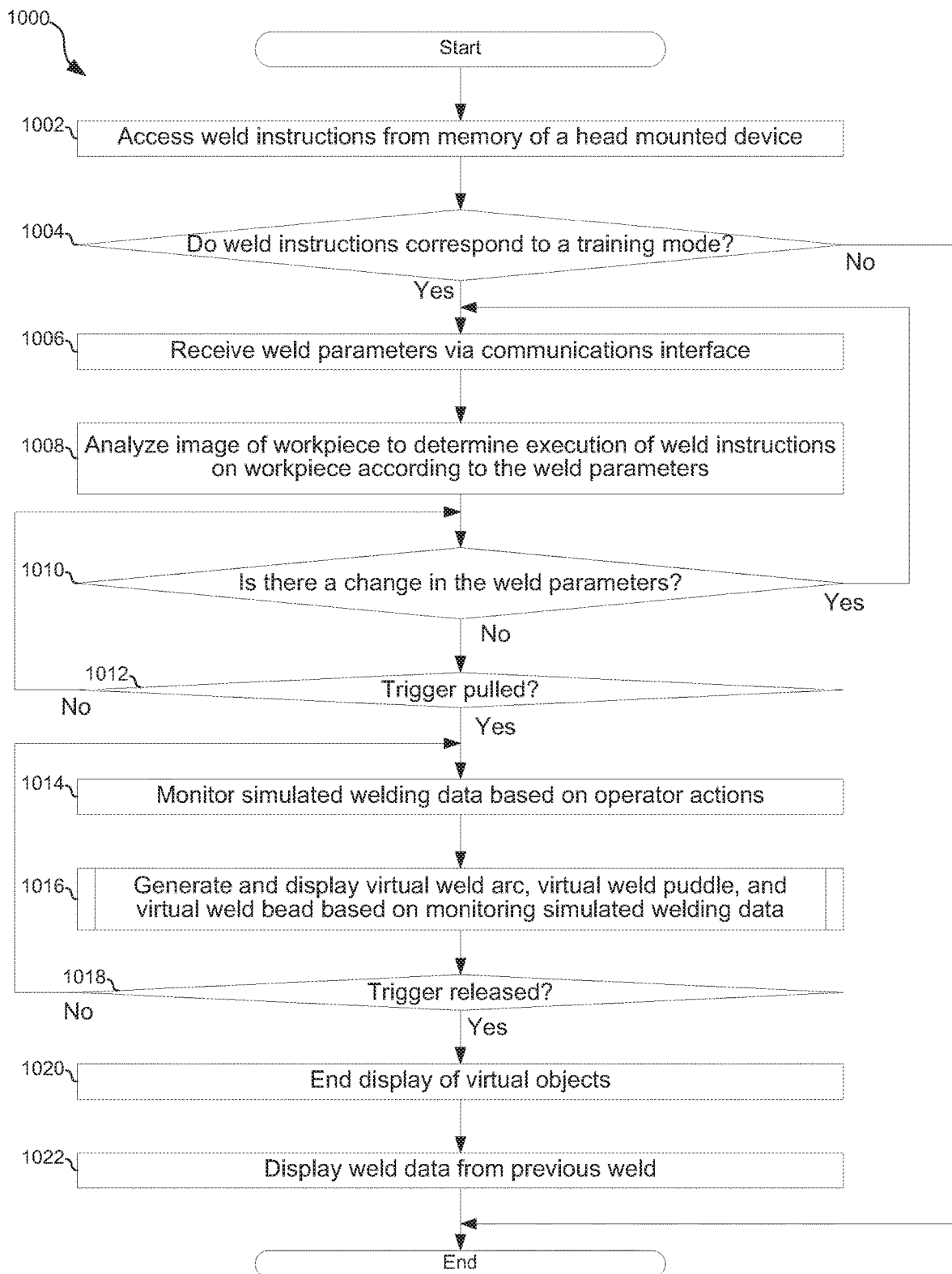
FIG. 10 is a flowchart representative of example machine readable instructions which may be executed by one or more processors to implement the head mounted device of FIGS. 1, 2A, 2B, and/or 2C to augment weld training with virtual objects.

FIG. 10 is a flowchart representative of example machine readable instructions 1000 which may be executed by one or more processors to implement the system 20 of FIGS. 1, 2A, and/or 2B to augment weld training with virtual objects.

At block 1002, the augmented reality controller 210 accesses weld instructions from the memory 211. For example, the instructions may be received and/or stored in the memory 211 prior to execution of the instructions 900. At block 1004, the augmented reality controller 210 determines whether the weld instructions correspond to a training mode. For example, the weld instructions may identify a training weld or a practice weld to be performed without an actual weld arc. The weld instructions may be received from a weld power source in response to the weld power source being placed in a simulation mode.

At block 1006, the augmented reality controller 210 receives weld parameter(s) via the communications interface 206 (e.g., from the weld power source). For example, the augmented reality controller 210 may receive the voltage, current, and/or process types set by the weld operator for the training weld. At block 1008, the augmented reality controller 210 analyzes an image of a workpiece taken by the camera(s) 216 to determine execution of the weld instructions on the workpiece according to the weld parameters. For example, the augmented reality controller 210 may generate and/or apply a weld model corresponding to the selected weld parameters using any characteristics that can be observed from the image of the workpiece.

At block 1010, the augmented reality controller 210 determines whether there have been any changes in the weld parameters. For example, the weld operator may adjust one or more of the weld parameters at the power supply (or via virtual controls presented by the system 20) prior to the training weld. If there have been any changes in the weld parameters (block 1010), the augmented reality controller 210 returns control to block 1006 to receive the new weld parameters.

If there have not been any changes in the weld parameters (block 1010), at block 1012 the augmented reality controller 210 determines whether the trigger of the weld torch has been pulled. For example, the augmented reality controller 210 may receive a trigger pull indication via the communications interface 206 from the power source when the weld operator pulls the trigger. If there has not been a trigger pull (block 1012), control returns to block 1010 to monitor for changes to the weld parameters.

If there has been a trigger pull (block 1012), at block 1014 the augmented reality controller 210 monitors simulated welding data based on the weld operator's actions. The simulated welding data may be received from the weld power source and/or identified via analysis of images from the camera(s) 216 and/or analysis of data from the sensor(s) 228.

At block 1016, the augmented reality controller 210 and the GPU/HPU 218 generate and display a virtual weld arc, a virtual weld puddle, and a virtual weld bead based on monitoring the simulated welding data. Block 1016 may be implemented using, for example, blocks 904-018 of FIG. 9, where the simulated objects are the virtual weld arc, the virtual weld puddle, and the virtual weld bead.

At block 1018, the augmented reality controller 210 determines whether the trigger has been released. For example, the augmented reality controller 210 may receive a trigger release indication via the communications interface 206 from the power source when the weld operator releases the trigger to stop the simulated weld. If there has not been a trigger release (block 1018), control returns to block 1014 to continue monitoring the simulated weld.

When the trigger has been released (block 1018), the augmented reality controller 210 and the GPU/HPU 218 end the display of the virtual objects (block 1020). At block 1022, the augmented reality controller 210 and the GPU/HPU 218 generate and display the weld data from the previous training weld for review by the weld operator and/or the weld operator's supervisor or trainer.

After displaying the weld data (block 1022), or if the weld instructions do not correspond to a training mode (block 1004), the example instructions 1000 of FIG. 10 end.

Figure 11A:
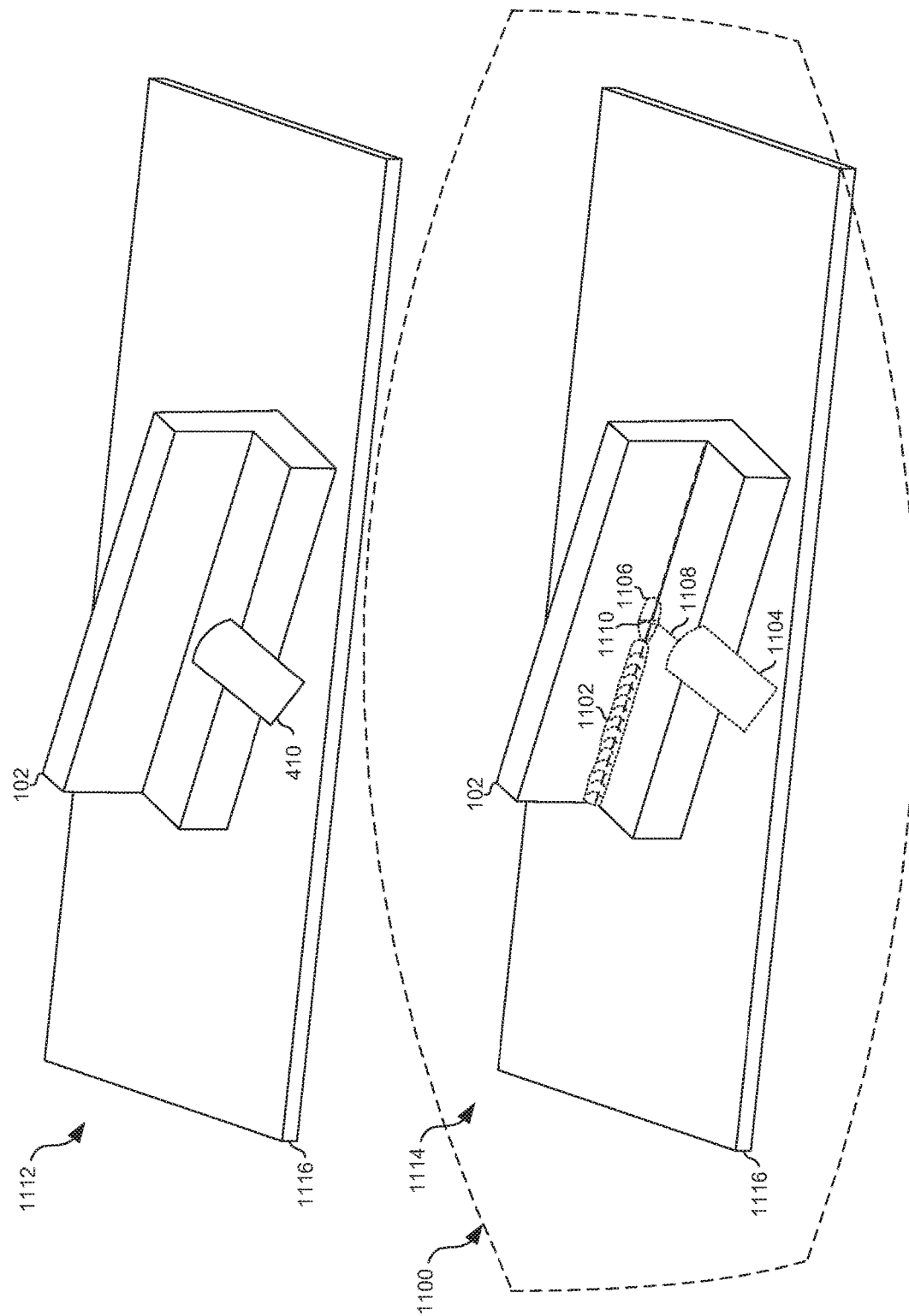
FIGS. 11A and 11B illustrate example interfaces displaying simulated objects overlaid on a real scene within fields of view corresponding to the interfaces in accordance with aspects of this disclosure.

FIG. 11A illustrates an example interface 1100 displaying simulated objects 1102, 1104, 1106, 1108, 1110 overlaid on a real scene 1112 within a field of view 1114 corresponding to the interface 1100. The example interface 1100 may be presented during a weld training session, in which an actual weld arc is not to be generated in the real scene 1112, but the appearance of the weld arc, weld puddle, and resulting weld are to be shown via the display.

The real scene 1112 includes the workpiece 102 and a workbench 1116, which are viewable by the operator through the interface 1100. The real scene 1112 also includes the torch 410. The augmented reality controller 210 of FIGS. 2A-2C uses the location of the torch 410 in the scene 1112 (e.g., determined by processing images of the weld scene 1112) to position the simulated objects 1102-1110, which include a simulated weld bead 1102, an outline 1104 of the torch 410, a simulated weld puddle 1106, a simulated electrode wire 1108, and a simulated arc 1110.

One or more of the simulated objects 1102-1110 may be replaced with actual objects in the real scene 1112 during an actual welding operation with a weld arc (e.g., training with an arc and/or an actual weld operation).

Figure 11B:
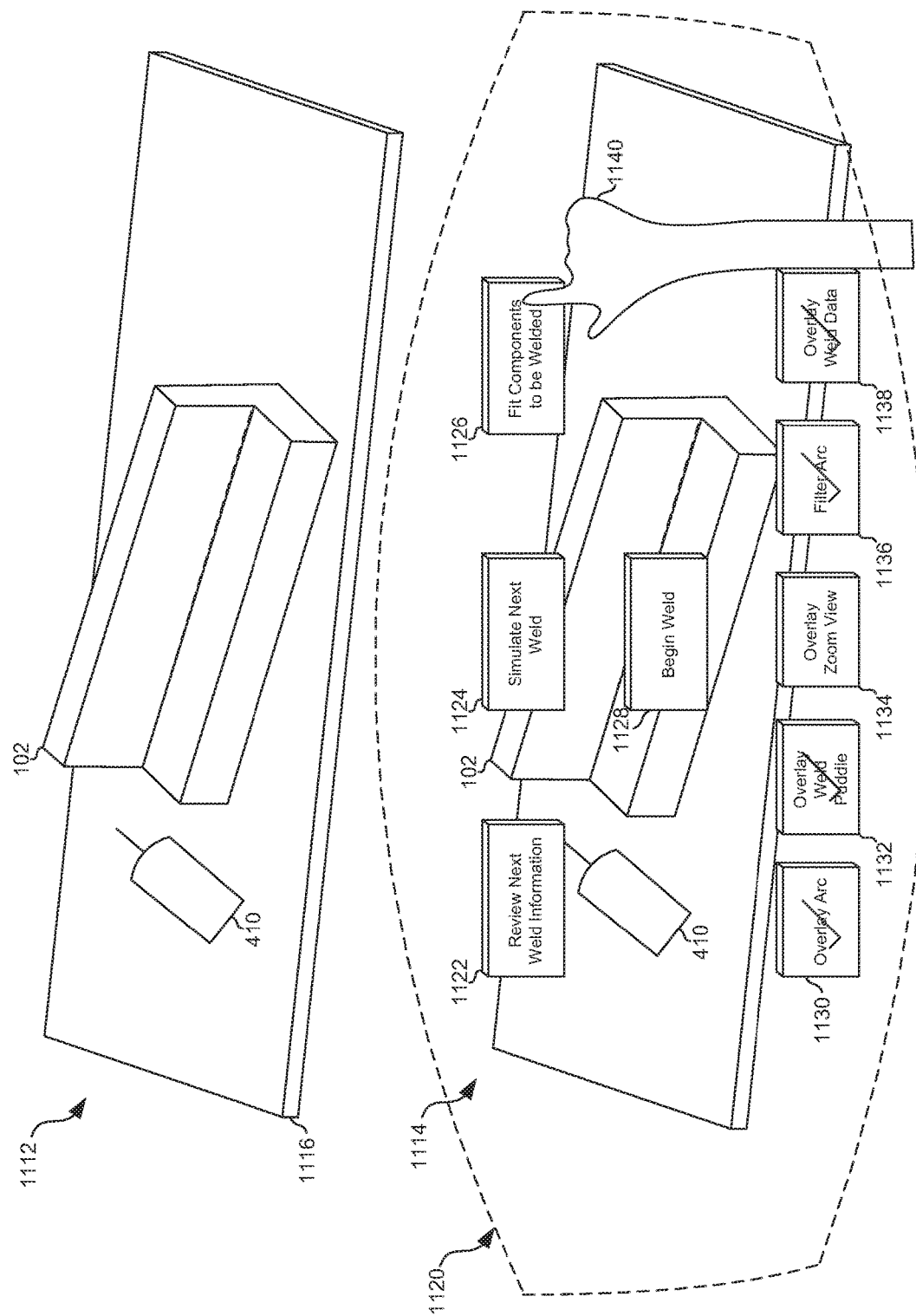

FIG. 11B illustrates another example interface 1120 displaying example graphics 1122-1138 for user selection via user input, overlaid on the real scene 1112 within the field of view 1114 corresponding to the interface 1120. The example graphics 1122-1138 may be, for example, menu items that are generated by the augmented reality controller 210 and presented via the near-eye display 222 to appear as though the graphics 1122-1138 are present in the scene 1112. However, the graphics 1122-1138 may be generated as a simpler overlay without the appearance of presence in the scene 1112. The example graphics 1122-1138 may be selected by the user via the user interface components 207, such as gesture recognition and/or voice commands. As illustrated in FIG. 11B, the user may simulate pushing of one or more of the graphics 1122-1138 using the user's hand 1140. The user receives visual feedback as to where the graphics 1122-1138 are relative to the user's hand 1140, and the augmented reality controller 210 identifies a selection of a graphic 1122-1138 based on the user simulating pushing of the graphic 1122-1138 as though the selected graphic 1122-1138 is a physical button.

The example "Review Next Weld Information" graphic 1122 causes the augmented reality controller 210 to display (e.g., overlay) weld information for a weld to be performed, such as the required equipment (e.g., consumable information, weld process information such as MIG, TIG, etc., voltage, current, travel speed, etc.). The example "Simulate Next Weld" graphic 1124 causes the augmented reality controller 210 to illustrate the next weld using the travel speed, arc length, and/or other characteristics of the weld for observation by the operator. In some examples, simulation of the weld includes tracking the user's movement of the weld torch and providing feedback to the user.

The example "Fit Components to be Welded" graphic 1126 causes the example augmented reality controller 210 to generate a simulation and/or animation of the welded components being fitted together and, in some examples, a simulation of the weld to be performed. The example "Begin Weld" graphic 1128 causes the augmented reality controller 210 to enter a welding mode, in which the augmented reality controller 210 displays one or more simulated objects in the field of view of the interface 1100 during a welding operation. Examples of such simulated objects are described in detail herein.

The example "Overlay Arc" graphic 1130 causes the augmented reality controller 210 to track and generate a simulated arc object in the location of the actual arc in the weld scene. In some examples, the overlaid arc blocks the user's view of the actual arc, which provides partial or complete protection to the user's eyes from arc light while permitting the user to view the location of the arc. The example "Overlay Weld Puddle" graphic 1132 causes the augmented reality controller 210 to generate and display a simulated weld puddle. The example "Overlay Zoom View" graphic 1134 causes the example augmented reality controller 210 to generate and display a zoomed in view of an aspect of the field of view 1114 (or, in some cases, not in the field of view). For example, the augmented reality controller 210 may provide a zoomed in view of the weld puddle as described above with reference to FIG. 4C.

The example "Filter Arc" graphic 1136 causes the augmented reality controller 210 to filter the light from the electrical arc using, for example, the near-eye display 222 and/or another filter controlled by the augmented reality controller 210. The example "Overlay Weld Data" graphic 1138 causes the augmented reality controller 210 to generate graphic(s) of weld data such as weld voltage, weld current, arc length, and/or travel speed for display to the user during a weld.

The example graphics 1130-1138 may be selected or deselected by the user, and the status of the graphics 1130-1138 is used by the augmented reality controller 210 to determine which simulated objects are to be generated by the augmented reality controller 210 for display. As shown in FIG. 11B, the graphics 1130, 1132, 1136, and 1138 are selected, while the graphic 1134 is deselected. Different presentations and/or manipulations of such graphics 1122-1138 may be used.

Figure 12A:
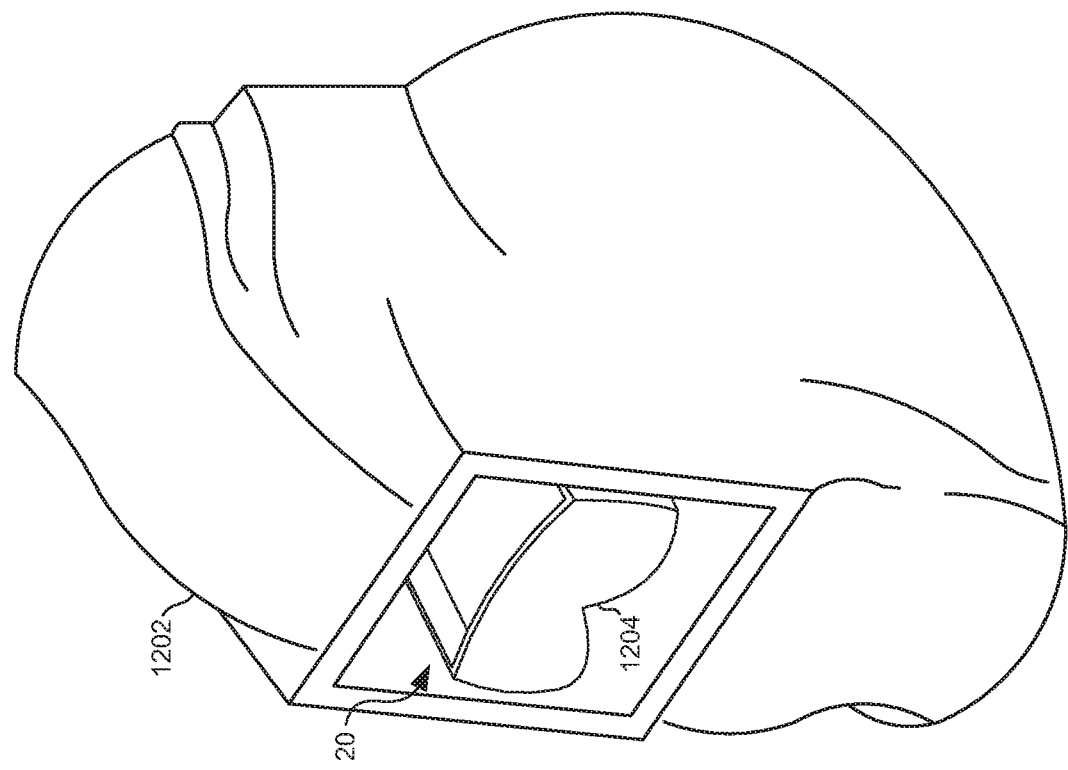
FIG. 12A illustrates an example head mounted system including a conventional welding helmet and a separate head mounted display wearable by an operator under the welding helmet in accordance with aspects of this disclosure.

FIG. 12A illustrates an example head mounted system 1200 including a conventional welding helmet 1202 and a separate head mounted display 1204 wearable by an operator under the welding helmet 1202. The example head mounted display 1204 may be the head mounted system 20 of FIGS. 2A, 2B, and/or 2C arranged a glasses-style or visor-type form factor. Examples that may be used to implement the head mounted display 1204 are described in U.S. Pat. No. 8,964,298, issued Feb. 24, 2015. The entirety of U.S. Pat. No. 8,964,298 is incorporated herein by reference. The head mounted display 1204 is configured to be put on by the user prior to donning the welding helmet 1202. In the example of FIG. 12A, the welding helmet may provide light protection features such as a passive or active darkening visor.

Figure 12B:
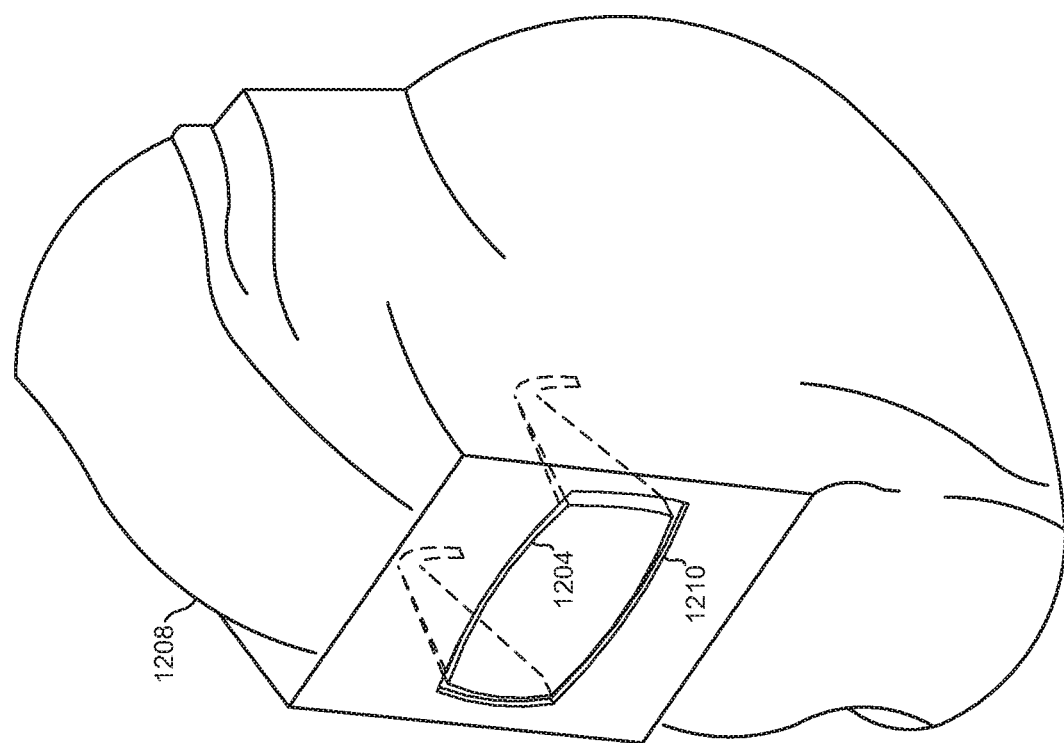
FIG. 12B illustrates another example head mounted system including an example welding helmet that has a viewing port sized to fit the head mounted display worn by an operator under the welding helmet.

FIG. 12B illustrates another example head mounted system 1206 including an example welding helmet 1208 that has a viewing port sized to fit the head mounted display 1204 worn by an operator under the welding helmet 1208. In the example of FIG. 12B, the welding helmet 1208 has a view port 1210 that is sized to permit the head mounted display 1204 to view through the view port 1210. The view port 1210 does not expose any other portion of the operator's face. In the example of FIG. 12B, the head mounted display 1204 may provide light protection features for the portion of the user's face covered by the head mounted display 1204.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

The present methods and/or systems may be realized in hardware, software, or a combination of hardware and software. The present methods and/or systems may be realized in a centralized fashion in at least one computing system, processors, and/or other logic circuits, or in a distributed fashion where different elements are spread across several interconnected computing systems, processors, and/or other logic circuits. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip such as field programmable gate arrays (FPGAs), a programmable logic device (PLD) or complex programmable logic device (CPLD), and/or a system-on-a-chip (SoC). Some implementations may comprise a non-transitory machine-readable (e.g., computer readable) medium (e.g., FLASH memory, optical disk, magnetic storage disk, or the like) having stored thereon one or more lines of code executable by a machine, thereby causing the machine to perform processes as described herein. As used herein, the term "non-transitory computer readable medium" is defined to include all types of computer readable storage media and to exclude propagating signals.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

What is claimed is:

1. A welding interface device, comprising:
an optical sensor to collect images of a weld environment;
an augmented reality controller configured to:
receive first instructions corresponding to a weld training operation;
analyze a first image of the weld environment collected by the optical sensor;
generate a weld model based on the first instructions and the first image;
initiate a simulated welding operation; and
monitor simulated weld data based on the weld model;
a graphics processing unit configured to generate at least one simulated object based on the monitored simulated weld data;
a semi-transparent display to present the rendered simulated object, at least a portion of the weld environment being observable through the semi-transparent display when the display is presenting the rendered simulated object; and
a communications interface, wherein the augmented reality controller is configured to receive the first instructions from a welding-type power supply via the communications interface.

2. The welding interface device of claim 1, further comprising a body, the optical sensor, the graphics processing unit, and the display being attached to the body, the body dimensioned to, when worn by a wearer, enable the wearer to further wear a welding helmet over the body, the welding helmet having a viewing port.

3. The welding interface device of claim 1, wherein the graphics processing unit comprises a holographic processor.

4. The welding interface device of claim 1, wherein the augmented reality controller comprises a first coprocessor and the graphics processing unit comprises a second coprocessor.

5. The welding user interface device of claim 1, wherein the at least one simulated object is one of a virtual weld puddle, a virtual weld bead, or a virtual weld arc.

6. The welding interface device of claim 1, wherein the display is a near-eye display.

7. The welding interface device of claim 1, wherein the graphics processing unit is configured to generate a virtual weld arc, a virtual weld puddle, and a virtual weld bead, and the semi-transparent display is configured to present the virtual weld arc, the virtual weld puddle, and the virtual weld bead.

8. The welding interface device of claim 1, wherein the simulated weld data is monitored in part based on additional images of the weld environment captured by the optical sensor.

9. The welding interface device of claim 1, further comprising a communications interface, wherein the augmented reality controller is configured to initiate the simulated welding operation based on a first signal received via the communications interface indicating that a trigger has been pulled.

10. The welding interface device of claim 9, wherein the augmented reality controller is configured to terminate the simulated welding operation based on a second signal received via the communications interface indicating that the trigger has been released.

11. The welding interface device of claim 1, wherein the semi-transparent display is configured to display the monitored simulated weld data during the simulated welding operation.

12. The welding interface device of claim 1, wherein the semi-transparent display is configured to display the monitored simulated weld data after the simulated welding operation is terminated.

13. The welding interface device of claim 1, wherein the optical sensor, the augmented reality controller, the graphics processing unit, and the display are integrated into a welding helmet.

14. The welding interface device of claim 1, further comprising a lens attached to the body, the lens to reduce an intensity of light occurring in the weld environment, the lens being arranged to provide the field of view to a wearer of the welding user interface device when the welding user interface device is worn by the wearer, the display being a near-eye display that is positioned between the lens and the wearer of the welding user interface device when worn by the wearer.

15. The welding interface device of claim 1, further including a communications controller to communicate a disable command in response to identifying a deviation from the first instructions.

16. The welding interface device of claim 1, further comprising an inertial measurement unit to provide at least one of movement information or orientation information, the augmented reality controller to determine a position of the simulated object on the at least one of the movement information or the orientation information.

17. The welding interface device of claim 1, wherein the graphics processing unit is configured to generate the simulated object as a three-dimensional stereographic image.

18. A welding interface device, comprising:
an optical sensor to collect images of a weld environment;
an augmented reality controller configured to:
    receive first instructions corresponding to a weld training operation;
    analyze a first image of the weld environment collected by the optical sensor;
    generate a weld model based on the first instructions and the first image;
    initiate a simulated welding operation; and
    monitor simulated weld data based on the weld model;
a graphics processing unit configured to generate at least one simulated object based on the monitored simulated weld data; and
a semi-transparent display to present the rendered simulated object, at least a portion of the weld environment being observable through the semi-transparent display when the display is presenting the rendered simulated object; and
a communications interface, wherein the simulated weld data is monitored in part based on information received from a welding-type power supply via the communications interface.

19. A welding interface device, comprising:
an optical sensor to collect images of a weld environment, wherein the optical sensor comprises:
    an illuminator to output a radiation at a first wavelength outside of an arc radiation spectrum:
    a time-of-flight sensor to collect the image of the weld environment at the first wavelength; and
    a bandpass filter to mitigate light at wavelengths other than the first wavelength;
an augmented reality controller configured to:
    receive first instructions corresponding to a weld training operation;
    analyze a first image of the weld environment collected by the optical sensor;
    generate a weld model based on the first instructions and the first image;
    initiate a simulated welding operation; and
    monitor simulated weld data based on the weld model;
a graphics processing unit configured to generate at least one simulated object based on the monitored simulated weld data; and
a semi-transparent display to present the rendered simulated object, at least a portion of the weld environment being observable through the semi-transparent display when the display is presenting the rendered simulated object.

* * * * *